United States Patent [19]

Freed et al.

[11] Patent Number: 5,597,719
[45] Date of Patent: Jan. 28, 1997

[54] INTERACTION OF RAF-1 AND 14-3-3 PROTEINS

[75] Inventors: Ellen Freed, Oakland; Rosamaria Ruggieri, San Francisco, both of Calif.

[73] Assignee: Onyx Pharmaceuticals, Inc., Richmond, Calif.

[21] Appl. No.: 276,151

[22] Filed: Jul. 14, 1994

[51] Int. Cl.⁶ .................................................. C12N 9/12
[52] U.S. Cl. ............................................................ 435/194
[58] Field of Search ................................................ 435/194

[56] References Cited

U.S. PATENT DOCUMENTS

| 5,238,916 | 8/1993 | Goldfarb et al. | 514/2 |
| 5,378,809 | 1/1995 | DiFiore et al. | 530/350 |
| 5,405,941 | 4/1995 | Johnson | 530/350 |

FOREIGN PATENT DOCUMENTS

WO91/02077  2/1991  WIPO.
WO94/29727  12/1994  WIPO.

OTHER PUBLICATIONS

Aitken et al. (1992) Trends Biochem. Sci. 17: 498–501.
Bonner et al. (1986) Nucl. Acids Res. 14(2): 1009–1015.
Ishikawa et al. (1987) Mol. Cell. Biol. 7(3): 1226–1232.
Kan et al. (1984) Proc. Natl. Acad. Sci. USA 81: 3000–3004.
Kan et al. (1984) Science 223:813–816.
Le Guellec et al. (1988) Nucl. Acids Res. 16(21): 10357.
Leffers et al. (1993) 231: 982–998.
Sutrave et al. (1984) Nature 309: 85–88.
Tahira et al. (1987) Nucl. Acids Res. 15(12): 4809–4820.
Xiao et al. (1995) Nature 376: 188–194.
Zupan et al. (1992) J. Biol. Chem. 267(13): 8707–8710.

Primary Examiner—Robert A. Wax
Assistant Examiner—Lisa J. Hobbs
Attorney, Agent, or Firm—Cooley Godward Castro Huddleson & Tatum

[57] ABSTRACT

Intermolecular interactions between Raf-1 and human 14-3-3 proteins which regulate Raf activity are identified. Compositions and method for identifying novel drugs which modulate Raf activity in vivo are provided.

6 Claims, 14 Drawing Sheets

Raf cDNA Map (1 > 2977)                    Site and Sequence
Enzymes:    All 373 enzymes (No Filter)
Settings:   Linear, Certain Sites Only, Standard Genetic Code

```
CCGAATGTGACCGCCTCCCGCTCCCTCACCCGCCGGGGGAGGAGAGCGGGGAGAAGCTGCCGCGAACGACAGGACG
GGCTTACACTGGGCGGAGGGCGAGGGAGTGGGCGGGCGCCCCTCCTCGCTCTTCGACGGGCTTGCTGTCCTGC    80
 P  N  V  T  A  S  R  S  L  T  R  R  G  E  E  E  R  A  S  C  R  R  T  T  G  R

TTGGGGCGGCCTGGCTCCCTCAGGTTTAAGAATTGTTTAAGCTGCATCAATGGAGCACATACAGGGAGCTTGGAAGACGA
AACCCCGCCGGACCGAGGGAGTCCAAATTCTTAACAAATTCGACGTAGTTACCTCGTGTATGTCCCTCGAACCTTCTGCT  160
 W  G  G  L  A  P  S  G  L  R  I  V    A  A  S  M  E  H  I  Q  G  A  W  K  T
                                       Raf-1 protein TCAGCAATGGTTTTGGATTCAAAGATGCCGTGTTTGATGGCTCCAGCTGCATCTCTCCTACAATAGTTCAGCAGTTTGGC
AGTCGTTACCAAAACCTAAGTTTCTACGGCACAAACTACCGAGGTCGACGTAGAGAGGATGTTATCAAGTCGTCAAACCG  240
 I  S  N  G  F  G  F  K  D  A  V  F  D  G  S  S  C  I  S  P  T  I  V  Q  Q  F  G
                    Raf-1 protein TATCAGCGCCGGGCATCAGATGATGGCAAACTCACAGATCCTTCTAAGACAAGCAACACTATCCGTGTTTTCTTGCCGAA
ATAGTCGCGGCCCGTAGTCTACTACCGTTTGAGTGTCTAGGAAGATTCTGTTCGTTGTGATAGGCACAAAAGAACGGCTT  320
 Y  Q  R  R  A  S  D  D  G  K  L  T  D  P  S  K  T  S  N  T  I  R  V  F  L  P  N
                    Raf-1 protein
```

FIG. IA-1

Raf c DNA Map (1 > 2977)                              Site and Sequence
CAAGCAAAGAACAGTGGTCAATGTGCGAATGAGCTTGCATGACTGCCTTATGAAAGCACTCAAGGTGAGGGGCC
                                                                          400
GTTCGTTTCTTGTCACCAGTTACACGCTTTACCTTACTGAACGTACTGACGGAATACTTTCGTGAGTTCCACTCCCGG
                              Raf-1 protein K  Q  R  T  V  V  N  V  R  N  G  M  S  L  H  D  C  L  M  K  A  L  K  V  R  G
TGCAACCAGAGTGTCGTGCAGTGTTCAGACTTCTCCACGAACACAAAGGTAAAAAAAGCACGCTTAGATTGGAATACTGAT
                                                                               480
ACGTTGGTCTCACGACACGTCACAAGTCTGAAGAGGTGCTTGTGTTTCCATTTTTTCGTGCGAATCTAACCTTATGACTA
                              Raf-1 protein L  Q  P  E  C  C  A  V  F  R  L  L  H  E  H  K  G  K  K  K  A  R  L  D  W  N  T  D
GCTGCGGTCTTTGATTGGAGAAGAACTTCAAGTAGAATTCCTGGATCATGTTCCCCTCACAACACACAACTTTGCTCGGAA
                                                                                 560
CGACGCCAGAAACTAACCTCTTCTTGAAGTTCATCTTAAGGACCTAGTACAAGGGGAGTGTTGTTGTTGAAACGAGCCTT
                              Raf-1 protein A  A  S  L  I  G  E  E  L  Q  V  D  F  L  D  H  V  P  L  T  T  H  N  F  A  R  K
GACGTTCCTGAAGCTTGCCTTCTGTGACATCTGTCAGAAATTCCTGCTCAATGGATTTCGATGTCAGACTTGTGGCTACA
                                                                                640
CTGCAAGGACTTCGAACGGAAGACACTGTAGACAGTCTTTAAGGACGAGTTACCTAAAGCTACAGTCTGAACACCGATGT
                              Raf-1 protein

```
Raf cDNA Map (1 >2977)              Site and Sequence
AATTTCATGAGCACTGTAGCACCAAAGTACCTACTATGTGTGTGGACTGGAGTAACATCAGAGTAACAACTCTTATTGTTTCCA
                                                                                    720
TTAAAGTACTCGTGACATCGTGGTTTCATGGATGATACACACCTGACCTCATTGTAGTCTGTTGAGAATAACAAAGGT
 K  F  H  E  H  C  S  T  K  V  P  T  M  C  V  D  W  S  N  I  R  Q  L  L  L  F  P
                          Raf-1 protein AATTCCACTATTGGTGATAGTGGAGTCCCAGCACTACCTTCTTTGACTATGCGTCGTATGCGAGAGTCTGTTTCCAGGAT
                                                                                    800
TTAAGGTGATAACCACTATCACCTCAGGGTCGTGATGGAAGAAACTGATACGCAGCATACGCTCTCAGACAAAGGTCCTA
 N  S  T  I  G  D  S  G  V  P  A  L  P  S  L  T  M  R  R  M  R  E  S  V  S  R  M
                          Raf-1 protein GCCTGTAGTTCTCAGCACAGATATTCTACACCTCACGCCTTCACCTTTAACACCTCCAGTCCCTCATCTGAAGGTTCCC
                                                                                    880
CGGACAATCAAGAGTCGTGTCTATAAGATGTGGAGTGCGGAAGTTGTGGAGGTCAGGGAGTAGACTTCCAAGGG
 P  V  S  S  Q  H  R  Y  S  T  P  H  A  F  T  F  N  T  S  S  P  S  S  E  G  S
                          Raf-1 protein TCTCCCAGAGGCAGAGGTCGACATCCACACCTGGTCAGCACCACGCTGCCTGTGGACAGCAGGATGATT
                                                                                    960
AGAGGGTCTCCGTTCTCCAGCTGTAGGTGTGATTACAGGTGTGCGCCACCTGTCGTGGCGACGGACACCTGTCGTCCTACTAA
 L  S  Q  R  Q  R  S  T  S  T  P  N  V  H  M  V  S  T  T  L  P  V  D  S  R  M  I
                          Raf-1 protein
```

```
Raf cDNA Map (1 >2977)                    Site and Sequence
GAGGATGCAATTCGAAGTCACAGCGAATCAGCCTTCACCTTCAGCCCTGTCCAGTAGCCCAACAATCTGAGCCCAACAGG
                                                                              1040
CTCCTACGTTAAGCTTCAGTGTCGCTTAGTCGGAGTGGAAGTCGGGACAGGTCATCGGGGTTGTTAGACTCGGGTTGTCC
                          Raf-1 protein
 E  D  A  I  R  S  H  S  E  S  A  S  S  P  S  A  L  S  S  S  P  N  N  L  S  P  T  G CTGGTCACAGCCGAAAAACCCCGTGCCAGCACACAGAGAGCGGGCACCAGTATCTGGGACCCAGGAGAAAACAAAATTA
                                                                              1120
GACCAGTGTCGGCTTTTGGGGCACGGTCGTGTTTCTCGCCCGTGGTCATAGACCCTGGGTCCTCTTTTTGTTTTAAT
                          Raf-1 protein
 W  S  Q  P  K  T  P  V  P  A  Q  R  E  R  A  P  V  S  G  T  Q  E  K  N  K  I GGCCTCGTGGACAGAGAGATTCAAGCTATTATTGGGAAATAGAAGCCAGTGAAGTGATGCTGTCCACTCGGATTGGGTCA
                                                                              1200
CCGGAGCACCTGTCTCTCTAAGTTCGATAATAACCCTTTATCTCGGTCACTTCACTACGACAGGTGAGCCTAACCCAGT
                          Raf-1 protein
 R  P  R  G  Q  R  D  S  S  Y  Y  W  E  I  E  A  S  E  V  M  L  S  T  R  I  G  S GGCTCTTTTGGAACTGTGTTTATAAGGGTAAATGGCACGGAGATGTTGCAGTAAAGATCCTAAAGGTTGTCGACCCAACCCC
                                                                              1280
CCGAGAAAACCTTGACACAAATATTCCCATTTACCGTGCCTCTACACGTCATTTCTAGGATTTCCAACAGCTGGGTTGGGG
                          Raf-1 protein
 G  S  F  G  T  V  Y  K  G  K  W  H  G  D  V  A  V  K  I  L  K  V  V  D  P  T  P
```

FIG. IB-2

```
Raf cDNA Map (1 > 2977)          Site and Sequence
AGAGCAAATTCCAGGCCTTCAGGAATGAGGTGGCTGTTCTGCGCAAAAACACGGCATGTGAACATTCTGCTTTCATGGGGT
                                                                                  1360
TCTCGTTAAGGTCCGGAAGTCCTTACTCCACCGACAAGAGCGTTTTGTGCCGTACACTTGTAAGACGAAAGTACCCA E  Q  F  Q  A  F  R  N  E  V  A  V  L  R  K  T  R  H  V  N  I  L  L  F  M  G
                              Raf-1 protein ACATGACAAAGGACAACCTGGCAATTGTGACCCAGTGGTGCGAGGGCAGCAGCCTCTACAAACACCTGCATGTCCAGGAG
                                                                                  1440
TGTACTGTTTCCTGTTGGACCGTTAACACTGGGTCACCACGCTCCCGTCGTCGGAGATGTTTGTGGACGTACAGGTCCTC Y  M  T  K  D  N  L  A  I  V  T  Q  W  C  E  G  S  S  L  Y  K  H  L  H  V  Q  E
                              Raf-1 protein ACCAAGTTTCAGATGTTCCAGCTAATTGACATTGCCCGGCAGACGGCTCAGGGAATGGACTATTTGCATGCAAAGAACAT
                                                                                  1520
TGGTTCAAAGTCTACAAGGTCGATTAACTGTAACGGGCCGTCTGCCGAGTCCCTTACCTGATAAACGTACGTTTCTTGTA T  K  F  Q  M  F  Q  L  I  D  I  A  R  Q  T  A  Q  G  M  D  Y  L  H  A  K  N  I
                              Raf-1 protein CATCCATAGAGACATGAAATCCAACAATATATTTCTCCATGAAGGCTTAACAGTGAAAATTGGAGATTTTGGTTTGGCAA
                                                                                  1600
GTAGGTATCTCTGTACTTTAGGTTGTTATATAAAGAGGTACTTCCGAATTGTCACTTTTAACCTCTAAAACCAAACCGTT I  H  R  D  M  K  S  N  N  I  F  L  H  E  G  L  T  V  K  I  G  D  F  G  L  A
                              Raf-1 protein
```

```
Raf cDNA Map (1>2977)        Site and Sequence
CAGTAAAGTCACGCTGGAGTGGTTCTCAGCAGGTTGAACAACCTACTGGCTCTGTCCTCTGGATGGCCCAGAGGTGATC
                                                                                1680
GTCATTTCAGTGCGACCTCACCAAGAGAGTCGTCCAACTTGTTGGATGACCAGGAGACAGGAGACCTACCGGGTCTCCACTAG Raf-1 protein
T  V  K  S  R  W  S  G  S  Q  Q  V  E  Q  P  T  G  S  V  L  W  M  A  P  E  V  I CGAATGCAGGATAACAACCCATTCAGTTTCCAGTCGGATGTCTACTCCTATGGCATCGTATTGTATGAACTGATGACGGG
                                                                                1760
GCTTACGTCCTATTGTTGGGTAAGTCAAAGGTCAGCCTACAGATGAGGATACCGTAGCATAACATACTTGACTACTGCCC Raf-1 protein
R  M  Q  D  N  N  P  F  S  F  Q  S  D  V  Y  S  Y  G  I  V  L  Y  E  L  M  T  G GGAGCTTCCTTATTCTCACATCAACAACCGAGATCAGATCATCTTCATGGTGGGCCGAGGATATGCCTCCCAGATCTTA
                                                                                1840
CCTCGAAGGAATAAGAGTGTAGTTGTTGGCTCTAGTCTAGTAGAAGTACCACCCGGCTCCTATACGGAGGGGTCTAGAAT Raf-1 protein
E  L  P  Y  S  H  I  N  N  R  D  Q  I  I  F  M  V  G  R  G  Y  A  S  P  D  L GTAAGCTATATAAGAACTGCCCCAAAGCAATGAAGAGGCTGGTAGCTGACTGTGTGAAGAAAGTAAAGGAAGAGAGGCCT
                                                                                1920
CATTCGATATATTCTTGACGGGGTTTCGTTACTTCTCCGACCATGACTGACACACTTCTTTCATTTCCTTCTCCGGA Raf-1 protein
S  K  L  Y  K  N  C  P  K  A  M  K  R  L  V  A  D  C  V  K  K  V  K  E  E  R  P
```

Raf cDNA Map (1>2977)                    Site and Sequence

CTTTTTCCCCAGATCCTGTCTTCCATTGAGCTGCTCCAACACTCTTACGAAGATCAACCGGAGCGCTTCCGAGCCATC
GAAAAGGGGTCTAGGACAGAAGTAACTCGACGAGGTTGTGAGAGATGGCTTCTAGTTGGCCTCGCGAAGGCTCGGTAG    2000
                              Raf-1 protein
L  F  P  Q  I  L  S  S  I  E  L  L  Q  H  S  L  P  K  I  N  R  S  A  S  E  P  S CTTGCATCGGGCAGCCCACACTGAGGATATCAATGCTTGCACGCTGACCACGTCCCGAGGCTGCTGTCTTCTAGTTGA
GAACGTAGCCCGTCGGGTGTGACTCCTATAGTTACGAACGTGCGACTGGTGCAGGGGCTCCGACGGACAGAAGATCAACT    2080
                    Raf-1 protein
L  H  R  A  A  H  T  E  D  I  N  A  C  T  L  T  T  S  P  R  L  P  V  F      L CTTTGCACCTGTCTTCAGGCTGCCAGGGGAGGAGGAGAAGCCAGCAGGCACCACTTTCTGCTCCCTTTCTCCAGAGGCA
GAAACGTGGACAGAAGTCCGACGGTCCCCTCCTCTTCGGTCGTCCGTGGTGAAAGACGAGGGAAAGAGGTCTCCGT    2160
T  L  H  L  S  S  G  C  Q  G  R  R  R  S  Q  Q  A  P  L  F  C  S  L  S  P  E  A GAACACACATGTTTTCAGAGAAGCTCTGCTAAGGACCTTTCTAGACTGCTCACAGGGCCTTAACTTCATGTTGCCTTCTTTTC
CTTGTGTACAAAGTCTCTTCGAGACGATTCCTGGAAGATCTGACGAGTGTCCCGGAATTGAAGTACAACGGAAGAAAAG    2240
E  H  M  F  S  E  K  L  C     G  P  S  R  L  L  T  G  P     L  H  V  A  F  F  S

FIG. ID-1

Raf cDNA Map (1 >2977)                                    Site and Sequence
TATCCCTTTGGGCCCTGGGAGAAGGAAGCCATTTGCAGTGCTGGTGTGTCCTGCTCCTCCCCACATTCCCATGCTCAA
ATAGGGAAACCCGGGACCCTCTTCCTTCGGTAAACGTCACGACCACACAGGACGAGGAGGGTGTAAGGGGTACGAGTT  2320
 I   P   L   G   P   G   R   R   K   P   F   A   V   L   V   C   P   A   P   S   P   H   S   P   C   S GGCCCAGCCTTCTGTAGATGCGCAAGTGGATGTTGATGGTAGTACAAAAAAGCAGGGCCCAGCCCAGCTGTTGGCTACA
CCGGGTCGGAAGACATCTACGCGTTCACCTACAATCATGTTTTTCGTCCCGGGTCGGGGTCGACAACCGATGT         2400
 R   P   S   L   L       M   R   K   W   M   L   M   Y   V   Q   K   A   G   A   Q   P   L   L   A   T TGAGTATTTAGAGGAAGTAAGGTAGCAGGCAGTCCAGCCCTGATGTGGAGACACATGGGATTTTGGAAATCAGCTTCTGG
ACTCATAAATCTCCTTCATTCCATCGTCCGTCAGGTCGGGACTACACCTCTGTACCCTAAAACCTTTAGTCGAAGACC   2480
 V   F   R   G   S   K   V   A   G   S   P   A   L   M   W   R   H   M   G   F   W   K   S   A   S   G AGGAATGCATGTCACAGGCGGGACTTTCTTCAGAGAGTGGTGCAGGCCCAGACATTTTGCACATAAGGCACCAAACAGCC
TCCTTACGTACAGTGTCCGCCCTGAAAGAAGTCTCTCACCACGTCCGGGCTCTGTAAAACGTGTATTCCGTGGTTGTCGG  2560
 G   M   H   V   T   G   G   T   F   F   R   E   W   C   S   A   R   H   F   A   H   K   A   P   N   S CAGGACTGCCGAGACTCTGGCCGCCGAAGGAGCCTGCTTTGGTACTATGGAACTTTTCTTAGGGGACACGTCCTCCTTT
GTCCTGACGGCTCTGAGACCGGCGGCTTCCTCGGACGAAACCATGATACCTTGAAAAGAATCCCCTGTGCAGGAGGAAA   2640
 P   G   L   P   R   L   W   P   P   E   G   A   C   F   G   T   M   E   L   F   L   G   D   T   S   S   F

FIG. 1D-2

Raf cDNA Map (1>2977)
Site and Sequence
                                                                                                                2720
CACAGCTTCTAAGGTGTCCAGTGCATTGGGATGGTTTTCCAGGCAAGGCACTCGGCCAATCCGCATCTCAGCCCCTCTCAG
GTGTCGAAGATTCCACAGGTCACGTAACCCTACCAAAAGGTCCGTTCCGTGAGCCGGTTAGGCGTAGAGTCGGGAGAGTC
 H  S  F  G  V  Q  C  I  G  M  V  F  Q  A  R  H  S  A  N  P  H  L  S  P  L  R 2800
GAGCAGTCTTCCATCATGCTGAATTTTGTCTTCCAGGAGCTGCCCCTATGGGGGCCGCAGGGCCAGCCTGTTTCTCT
CTCGTCAGAAGGTAGTACGACTTAAAACAGAAGGTCCTCGACGGGATACCCCGGCGTCCCGGTCGGACAAAGAGA
 S  S  L  P  S  C     I  L  S  S  R  S  C  P  Y  G  A  G  R  R  A  S  L  F  L 2880
AACAAACAAACAAACAGCCTTGTTTCTCTAGTCACATCATGTATACAAGGAAGCCAGGAATACAGGTTTTCTTG
TTGTTTGTTTGTTTGTCGGAACAAAGAGATCAGTGTAGTACACATATGTTCCTTCGGTCCTTATGTCCAAAAGAAC
 Q  T  N  K  Q  T  A  L  F  L     S  H  H  V  Y  T  R  K  P  G  I  Q  V  F  L 2960
ATGATTTGGGTTTTAATTTTGTTTTTTATTGCACCTGACAAAAATACAGTTATCTGATGGTCCCTCAATTATGTTATTTTAA
TACTAAACCCAAAATTAAAACAAAAAATAACGTGGACTGTTTATGTCAATAGACTACCAGGGAGTTAATACAATAAAATT
 M  I  W  V  L  I  L  F  L  L  H  L  T  K  Y  S  Y  L  M  V  P  Q  L  C  Y  F  N

TAAAATAAAATTAAATTT    2977
ATTTTATTTTAATTTAAA    ↑
 K  I  N                 ↑

FIG. IE

Full length Raf-1

| | | | | |
|---|---|---|---|---|
| MEHIQGAWKT | ISNGFGFKDA | VFDGSSCISP | TIVQQFGYQR | RASDDGKLTD |
| PSKTSNTIRV | FLPNKQRTVV | NVRNGMSLHD | CLMKALKVRG | LQPECCAVFR |
| LLHEHKGKKA | RLDWNTDAAS | LIGEELQVDF | LDHVPLTTHN | FARKTFLKLA |
| FCDICQKFLL | NGFRCQTCGY | KFHEHCSTKV | PTMCVDWSNI | RQLLLFPNST |
| IGDSGVPALP | SLTMRRMRES | VSRMPVSSQH | RYSTPHAFTF | NTSSPSSEGS |
| LSQRQRSTST | PNVHMVSTTL | PVDSRMIEDA | IRSHSESASP | SALSSSPNNL |
| SPTGWSQPKT | PVPAQRERAP | VSGTQEKNKI | RPRGQRDSSY | YWEIEASEVM |
| LSTRIGSGSF | GTVYKGKWHG | DVAVKILKVV | DPTPEQFQAF | RNEVAVLRKT |
| RHVNILLFMG | YMTKDNLAIV | TQWCEGSSLY | KHLHVQETKF | QMFQLIDIAR |
| QTAQGMDYLH | AKNIIHRDMK | SNNIFLHEGL | TVKIGDFGLA | TVKSRWSGSQ |
| QVEQPTGSVL | WMAPEVIRMQ | DNNPFSFQSD | VYSYGIVLYE | LMTGELPYSH |
| INNRDQIIFM | VGRGYASPDL | SKLYKNCPKA | MKRLVADCVK | KVKEERPLFP |
| QILSSIELLQ | HSLPKINRSA | SEPSLHRAAH | TEDINACTLT | TSPRLPVF |

Raf 1-197

| | | | | |
|---|---|---|---|---|
| MEHIQGAWKT | ISNGFGFKDA | VFDGSSCISP | TIVQQFGYQR | RASDDGKLTD |
| PSKTSNTIRV | FLPNKQRTVV | NVRNGMSLHD | CLMKALKVRG | LQPECCAVFR |
| LLHEHKGKKA | RLDWNTDAAS | LIGEELQVDF | LDHVPLTTHN | FARKTFLKLA |
| FCDICQKFLL | NGFRCQTCGY | KFHEHCSTKV | PTMCVDWSNI | RQLLLFP |

Raf 186-332

| | | | | |
|---|---|---|---|---|
| | DWSNI | RQLLLFPNST | IGDSGVPALP | SLTMRRMRES | VSRMPVSSQH |
| RYSTPHAFTF | NTSSPSSEGS | LSQRQRSTST | PNVHMVSTTL | PVDSRMIEDA |
| IRSHSESASP | SALSSSPNNL | SPTGWSQPKT | PVPAQRERAP | VSGTQEKNKI |
| RP | | | | |

Raf 303-648

| | | | | |
|---|---|---|---|---|
| | TGWSQPKT | PVPAQRERAP | VSGTQEKNKI | RPRGQRDSSY | YWEIEASEVM |
| LSTRIGSGSF | GTVYKGKWHG | DVAVKILKVV | DPTPEQFQAF | RNEVAVLRKT |
| RHVNILLFMG | YMTKDNLAIV | TQWCEGSSLY | KHLHVQETKF | QMFQLIDIAR |
| QTAQGMDYLH | AKNIIHRDMK | SNNIFLHEGL | TVKIGDFGLA | TVKSRWSGSQ |
| QVEQPTGSVL | WMAPEVIRMQ | DNNPFSFQSD | VYSYGIVLYE | LMTGELPYSH |
| INNRDQIIFM | VGRGYASPDL | SKLYKNCPKA | MKRLVADCVK | KVKEERPLFP |
| QILSSIELLQ | HSLPKINRSA | SEPSLHRAAH | TEDINACTLT | TSPRLPVF |

FIG. 1F 14-3-3 β nucleotide sequence

```
1    taccgccacc gccgccgccg attccggagc cggggtagtc gccgccgccg ccgccgccgc
61   tgcagccact gcaggcaccg ctgccgccgc ctgagtagtg taccgccacc gccgccgccg
121  attccggagc cggggtagtc gccgccgccg ccgccgccgc tgcagccact gcaggcaccg
181  ctgccgccgc ctgagtagtg ggcttaggaa ggaagaggtc atctcgctcg gagcttcgct
241  cggaagggtc tttgttccct gcagccctcc cacggcagag tctccagaga tttgggccgc
301  tacaaaaagt gcattttgcc cattcggctg tggatagaga agcaggaaga gcactggact
361  tggagtcagg gaATGacaat ggataaaagt gagctggtac agaaagccaa actcgctgag
421  caggctgagc gctatgatga tatggctgca gccatgaagg cagtcacaga acaggggcat
481  gaactctcca acgaagagag aaatctgctc tctgttgcct acaagaatgt ggtaggcgcc
541  cgccgctctt cctggcgtgt catctccagc attgagcaga aacagagag gaatgagaag
601  aagcagcaga tgggcaaaga gtaccgtgag aagatagagg cagaactgca ggacatctgc
661  aatgatgttc tggagctgtt ggacaaatat cttattccca atgctacaca accagaaagt
721  aaggtgttct acttgaaaat gaaggagat tattttaggt atctttctga agtggcatct
781  ggagacaaca aacaaaccac tgtgtcgaac tcccagcagg cttaccagga agcatttgaa
841  attagtaaga agaaatgca gcctacacac ccaattcgtc ttggtctggc actaaatttc
901  tcagtctttt actatgagat tctaaactct cctgaaaagg cctgtagcct ggcaaaaacg
961  gcatttgatg aagcaattgc tgaattggat acgctgaatg aagagtctta taagacagc
1021 actctgatca tgcagttact tagggacaat ctcactctgt ggacatcgga aaaccaggga
1081 gacgaaggag acgctgggga gggagagaac TAAtgtttct cgtgctttgt gatctgtcca
1141 gtgtcactct gtaccctcaa catatatccc ttgtgcgata aaaaaaaaa aaaaaaaaa
1201 aaaaaaaaaa aaa
```

FIG. 2A

Human 14-3-3 β

```
MTMDKSELVQ  KAKLAEQAER  YDDMAAAMKA  VTEQGHELSN  EERNLLSVAY
KNVVGARRSS  WRVISSIEQK  TERNEKKQQM  GKEYREKIEA  ELQDICNDVL
ELLDKYLIPN  ATQPESKVFY  LKMKGDYFRY  LSEVASGDNK  QTTVSNSQQA
YQEAFEISKK  EMQPTHPIRL  GLALNFSVFY  YEILNSPEKA  CSLAKTAFDE
AIAELDTLNE  ESYKDSTLIM  QLLRDNLTLW  TSENQGDEGD  AGEGEN.
```

FIG. 2B 14-3-3 ζ cDNA

```
   1  gcccactccc accgccagct ggaaccctgg ggactacgac gtccctcaaa ccttgcttct
  61  aggagataaa aagaacatcc agtcATGgat aaaaatgagc tggttcagaa ggccaaactg
 121  gccgagcagg ctgagcgata tgatgacatg gcagcctgca tgaagtctgt aactgagcaa
 181  ggagctgaat tatccaatga ggagaggaat cttctctcag ttgcttataa aaatgttgta
 241  ggagcccgta ggtcatcttg gagggtcgtc tcaagtattg aacaaaagac ggaaggtgct
 301  gagaaaaaac agcagatggc tcgagaatac agagagaaaa ttgagacgga gctaagagat
 361  atctgcaatg atgtactgtc tcttttggaa aagttcttga tccccaatgc ttcacaagca
 421  gagagcaaag tcttctattt gaaaatgaaa ggagattact accgttactt ggctgaggtt
 481  gccgctggtg atgacaagaa agggattgtc gatcagtcac aacaagcata ccaagaagct
 541  tttgaaatca gcaaaaagga aatgcaacca acacatccta tcagactggg tctggcccct
 601  aacttctctg tgttctatta tgagattctg aactccccag agaaagcctg ctctcttgca
 661  aagacagctt ttgatgaagc cattgctgaa cttgatacat taagtgaaga gtcatacaaa
 721  gacagcacgc taataatgca attactgaga gacaacttga cattgtggac atcggatacc
 781  caaggagacg aagctgaagc aggagaagga ggggaaaaaT AAccggcctt ccaacttttg
 841  tctgcctcat tctaaaattt acacagtaga ccatttgtca tccatgctgt cccacaaata
 901  gttttttgtt tacgatttat gacaggttta tgttacttct atttgaattt ctatatttcc
 961  catgtggttt ttatgtttaa tattagggga gtagagccag ttaacattta gggagttatc
1021  tgttttcatc ttgaggtggc caatatgggg atgtggaatt tttatacaag ttataagtgt
1081  ttggcatagt acttttggta cattgtggct tcaaagggc cagtgtaaaa ctgcttccat
1141  gtctaagcaa agaaaactgc ctacatactg gtttgtcctg gcggggaata aaagggatca
1201  ttggttccag tcacaggtgt agtaattgtg ggtactttaa ggtttggagc acttacaagg
1261  ctgtggtaga atcatacccc atggatacca catattaaac catgtatatc tgtggaatac
1321  tcaatgtgta cacctttgac tacagctgca gaagtgttcc tttagacaaa gttgtgaccc
1381  attttactct ggataagggc agaaacggtt cacattccat tatttgtaaa gttacctgct
1441  gttagctttc attattttg ctacactcat tttatttgta tttaaatgtt ttaggcaacc
```

FIG. 3A-1

4-3-3 ζ cDNA

```
1501 taagaacaaa tgtaaaagta aagatgcagg aaaaatgaat tgcttggtat tcattacttc
1561 atgtatatca agcacagcag taaaacaaaa acccatgtat ttaactttt tttaggattt
1621 ttgcttttgt gatttttttt tttttttttt gatacttgcc taacatgcat gtgctgtaaa
1681 aatagttaac agggaaataa cttgagatga tggctagctt tgtttaatgt cttatgaaat
1741 tttcatgaac aatccaagca taattgttaa gaacacgtgt attaaattca tgtaagtgga
1801 ataaaagttt tatgaatgga cttttcaact actttctcta cagcttttca tgtaaattag
1861 tcttggttct gaaacttctc taaaggaaat tgtacattct ttgaaattta ttccttattc
1921 cctcttggca gctaatgggc tcttaccaag tttaaacaca aaatttatca taacaaaaat
1981 actactaata taactactgt ttccatgtcc catgatcccc tctcttcctc cccaccctga
2041 aaaaaatgag ttcctatttt ttctgggaga gggggggatt gattagaaaa aaatgtagtg
2101 tgttccattt aaaatttggg catatggcat tttctaactt aggaagccac aatgttcttg
2161 gcccatcatg acattgggta gcattaactg taagttttgt gcttccaaat cacttttgg
2221 tttttaagaa tttcttgata ctcttatagc ctgccttcaa ttttgatcct ttattctttc
2281 tatttgtcag gtgcacaaga ttaccttcct gttttagcct tctgtcttgt caccaaccat
2341 tcttacttgg tggccatgta cttggaaaaa ggccgcatga tctttctggc tccactcagt
2401 gtctaaggca ccctgcttcc tttgcttgca tcccacagac tatttccctc atcctattta
2461 ctgcagcaaa tctctcctta gttgatgaga ctgtgtttat ctccctttaa aaccctacct
2521 atcctgaatg gtctgtcatt gtctgccttt aaaatccttc ctctttcttc ctcctctatt
2581 ctctaaataa tgatggggct aagttatacc caaagctcac tttacaaaat atttcctcag
2641 tactttgcag aaaacaccaa acaaaaatgc cattttaaaa aaggtgtatt ttttcttta
2701 gaatgtaagc tcctcaagag cagggacaat gttttctgta tgttctattg tgcctagtac
2761 actgtaaatg ctcaataaat attgatgatg ggaggcagtg agtcttgatg ataagggtga
2821 gaaactgaaa tccc
```

FIG. 3A-2

Human 14-3-3 ζ

```
MDKNELVQKA  KLAEQAERYD  DMAACMKSVT  EQGAELSNEE  RNLLSVAYKN
VVGARRSSWR  VVSSIEQKTE  GAEKKQQMAR  EYREKIETEL  RDICNDVLSL
LEKFLIPNAS  QAESKVFYLK  MKGDYYRYLA  EVAAGDDKKG  IVDQSQQAYQ
EAFEISKKEM  QPTHPIRLGL  ALNFSVFYYE  ILNSPEKACS  LAKTAFDEAI
AELDTLSEES  YKDSTLIMQL  LRDNLTLWTS  DTQGDEAEAG  EGGEN.
```

FIG. 3B

INTERACTION OF RAF-1 AND 14-3-3 PROTEINS

TECHNICAL FIELD

The invention provides compositions and methods for treating or preventing neoplasia in human and veterinary patients, compositions and methods for screening a library of agents for pharmacological activity in regulating cell proliferation and/or cell differentiation, compositions and methods for modulation of a transformed cell phenotype in vitro, including use in bioprocess control and as commercial laboratory reagents.

BACKGROUND

Neoplastic Disease

Neoplasia is the relatively autonomous proliferation of cells, whereby cells partially or totally escape physiological control mechanisms that ordinarily constrain cell proliferation and regulate cell differentiation. The proliferation of normal cells is believed regulated by growth-promoting proto-oncogenes counterbalanced by growth-constraining tumor-suppressor genes. Mutations that potentiate the activities of proto-oncogenes can create the oncogenes that force the deregulated growth of neoplastic cells. Conversely, genetic lesions that inactivate tumor suppressor genes, generally through mutation(s) that lead to a cell being homozygous for the inactivated tumor suppressor allele, can liberate the cell from the normal replicative constraints imposed by these genes. Often, an inactivated tumor suppressor gene in combination with the formation of an activated oncogene (i.e., a proto-oncogene containing an activating structural or regulatory mutation) can yield a neoplastic cell capable of essentially unconstrained growth (i.e., a transformed cell).

Many pathological conditions result, at least in part, from aberrant control of cell proliferation, differentiation, and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

The precise molecular pathways and secondary changes leading to malignant transformation for many cell types are not entirely clear.

Oncogenic transformation of cells leads to a number of changes in cellular metabolism, physiology, and morphology. One characteristic alteration of oncogenically transformed cells is a loss of responsiveness to constraints on cell proliferation and differentiation normally imposed through one or more signalling pathway(s) which comprise proteins encoded by proto-oncogenes. For example, proteins encoded by ras genes serve as essential transducers of diverse physiological signals, and mutationally altered ras gene products are important contributors to the neoplastic phenotype. The 21 kilodalton protein encoded by the $ras^H$ gene, referred to as $p21^{ras}$, is involved in the signal transduction of various factors controlling cell proliferation, differentiation, and oncogenesis.

raf-1 Signaling Pathway

Investigations have revealed several proteins that function upstream and downstream of $p21^{ras}$ in signalling pathways. In particular, a protein encoded by the raf-1 proto-oncogene functions downstream of $p21^{ras}$ and is implicated in several other signalling pathways, including T cell receptor stimulation (Siegel et al. (1993) *J. Immunol.* 151: 4116; Wotton et al. (1993) *J. Biol. Chem.* 268: 17975; Prasad KV and Rudd CE (1992) *Mol. Cell. Biol.* 12: 5260), muscarinic m2 receptor stimulation (Winitz et al. (1993) *J. Biol. Chem.* 268: 19196), TPA/protein kinase C-stimulation and TNF-α receptor stimulation (Finco et al. (1993) *J. Biol. Chem.* 268: 17676; Sozeri et al. (1992) *Oncogene* 7: 2259), IL-2 receptor stimulation (Turner et al. (1993) *Proc. Natl. Acad. Sci. (USA).* 90: 5544), nerve growth factor receptor stimulation (Ohmichi et al. (1992) *J. Biol. Chem.* 267: 14604), erythropoietin-mediated proliferation (Carroll et al. (1991) *J. Biol. Chem.* 266: 14964), and various mitogenic signalling pathways such as EGF and PDGF receptor stimulation (Kizaka-Kondoh et al. (1992) *Mol. Cell. Biol.* 12: 5078; Baccarini et al. (1991) *J. Biol. Chem.* 266: 10941) and insulin stimulation (Lee et al. (1991) *J. Biol. Chem.* 266: 10351).

The raf-1 protein is a serine/threonine kinase that is structurally related to the protein kinase C (PKC) family, and is essential in cell growth and differentiation. A variety of upstream signaling pathways lead to raf-1, which exhibits an enhanced kinase activity when activated via an upstream signaling pathway. The exact biochemical alterations that define activation of raf-1 have not been rigorously defined. The raf-1 protein and $p21^{ras}$ have been found to physically associate with each other via the amino-terminal portion of raf-1, but this association is not itself sufficient to activate raf-1 kinase activity (Fabian et al. (1993) *Mol. Cell. Biol.* 13: 7170; Traverse et al. (1993) Oncogene 8: 3175; Koide et al. (1993) *Proc. Natl. Acad. Sci. (USA)* 90: 8683; Warne et al. (1993) *Nature* 364: 352; Zhang et al. (1993) *Nature* 364: 308). The portions of raf-1 which confer binding specificity towards other proteins remains to be elucidated, as does the molecular identification of such other raf-1 binding proteins. Recent studies of growth factor signal transduction pathways have shown that raf-1 functions downstream of several activated tyrosine kinases as well as $p21^{ras}$ and functions upstream of mitogen-activated protein kinase (MAP kinase). Thus, in addition to $p21^{ras}$, a variety of oncogene proteins and receptors having tyrosine kinase activity can activate the kinase activity of raf-1 towards various substrates, which then modulate downstream signalling (Gardner et al. (1993) *J. Biol. Chem.* 268: 17896). The raf-1 protein becomes phosphorylated on tyrosine residue(s) in response to upstream signals, such as by growth factor stimulation, and this phosphorylation is involved in the activation of raf-1 kinase activity (Fabian et al. (1993) op.cit.; Morrison et al. (1993) *J. Biol. Chem.* 268: 17309). Inhibiting raf-1 function blocks mitogen-activated protein kinase activation by growth factors and $p21^{ras}$ (Schaap et al. (1993) *J. Biol. Chem.* 268; 20232; Samuels et al. (1993) *Mol. Cell. Biol.* 13: 6241).

Once activated, raf-1 manifests a serine/threonine kinase activity which acts on a variety of polypeptide substrates that comprise one or more downstream signaling pathways. Recently, oncogenically activated raf-1 has been demonstrated to activate MAP kinase, which leads to the phosphorylation and activation of various MAP kinases, such as the extracellular signal-regulated kinases ERK1 and ERK2 (Howe et al. (1992) *Cell* 71: 335; Kyriakis et al. (1992)

Nature 358: 417). MAP kinases appears to be a central component of many different signal transduction pathways, and activation of MAP kinases has been shown to direct phosphorylation of transcription factors, such as c-myc, c-jun, and p62$^{TcF}$ (Gille et al. (1992) *Nature* 358: 414; Alvarez et al. (1991) *J. Biol. Chem.* 266; 15277; Pulverer et al. (1991) *Nature* 353: 670; Seth et al. (1991) *J. Biol. Chem.* 266: 23521) and activation of other kinases, such as p90$^{rsk}$(Sturgill et al. (1988) *Nature* 334; 715; Chung et al (1991) *Proc. Natl. Acad. Sci.* (USA) 88: 4981) and MAP-KAP kinase 2 (Stokoe et al. (1992) *EMBO J.* 11: 3985). Macdonald et al. (1993) *Mol. Cell. Biol.* 13:6615 have shown that MEK (MAP/ERK kinase) is a direct phosphorylation substrate of raf-1, and that phosphorylation of MEK by raf-1 is sufficient for MEK activation.

Since many of the signaling pathway(s) which are mediated by activation of the kinase activity of raf-1 are involved in control of cell proliferation and oncogenic transformation, it would be desirable to identify other physiologically relevant proteins to which raf-1 binds. Moreover, it would be desirable to have agents which modulate the activity of raf-1, such as agents which interfere with the binding of raf-1 to other proteins, particularly inhibiting binding of raf-1 to proteins involved in the control of the cell cycle and/or cell differentiation. Such raf-1 blocking agents can be administered to a human or veterinary patient in a pharmaceutically acceptable form and in a therapeutically effective dosage for prophylaxis and therapy of diseases, including neoplasia, hyperplasia, and other pathological conditions related to elevated or prolonged raf-1 activity. Preferably, such raf-1 blocking agents will be small molecules or peptidomimetics which have advantageous pharmacokinetic properties, such as a desirable half-life, low toxicity, ready deliverability to various tissues and organs, facile passage across cell membranes to gain access to intracellular raf-1, and the like. Advantageously, such raf-1 blocking agents will also find use as commercial reagents, for example, to modulate a cultured cell phenotype for laboratory purposes and/or for bioprocess control (e.g., to prevent excessive cell proliferation in a bioreactor culture), and the like.

Despite progress in developing a more defined model of the molecular mechanisms underlying the transformed phenotype and neoplasia, few significant therapeutic methods applicable to treating cancer beyond conventional chemotherapy have resulted. The observation that aberrant raf-1 function is frequently correlated with neoplasia supports a model wherein raf-1 protein is involved in control of cell proliferation, and may be involved in one or more signalling pathways that transduce growth regulatory signals. If such a model were correct, raf-1 and biological macromolecules (i.e., proteins) that specifically interact with raf-1 would be candidate targets for therapeutic manipulation. For example and not limitation, if a hypothetical protein X bound to raf-1 forming a complex and thereby stimulated (or alternatively, inhibited) neoplastic growth of cells, agents that would selectively inhibit (or alternatively, augment) formation of the protein X: raf-1 complex or otherwise modulate raf-1 activity may be candidate antineoplastic agents.

The identification of proteins that interact with raf-1 protein provide a basis for screening assays for identifying agents that specifically interfere with the intermolecular association between raf-1 protein and such interacting proteins. These screening assays can be used to identify candidate raf-1 modulating agents that can serve as candidate therapeutic agents. Such raf-1 modulating agents can provide novel chemotherapeutic agents for treatment of neoplasia, cell proliferative conditions, arthritis, inflammation, autoimmune diseases, and the like. The present invention fulfills these and other needs.

Based on the foregoing, it is clear that a need exists for agents that inhibit raf-1 (e.g., inhibit binding of raf-1 to other proteins involved in signal transduction and/or growth control) and which are pharmaceutically acceptable for use in humans and veterinary patients to treat diseases characterized by undesired raf-1 activity, such as cancer, hyperplasia, and the like. Thus, it is an object of the invention herein to provide such raf-1 blocking agents, compositions of such agents, methods of treating diseases resulting from excessive raf-1 activation (e.g., neoplasia, hyperplasia), and novel pharmaceutical compositions comprising a raf-1 inhibitory agent in combination with one or more additional antineoplastic agents.

14-3-3 Proteins

A family of proteins known as 14-3-3 proteins have been identified by investigators studying a broad range of biological systems, including plants, yeast, mammals, and invertebrates (Martens et al. (1992) *Biochem Biophys Res Commun* 184: 1456; van Heusden et al. (1992) *FEBS Lett* 302: 145; Prasad et al. (1992) *Cell Growth Differ* 3: 507; Zupan et al. (1992) *J. Biol Chem* 267: 8707; Leffers et al. (1993) *J. Mol Biol* 231: 982; McConnell JE and Hodges PE (1993) *Gene* 126: 293).

An outstanding feature of this family is the extraordinarily high sequence conservation observed between members. 14-3-3 proteins are apparently ubiquitous eukaryotic proteins that comprise a large number of isoforms, most of which contain an N-acetylated amino-terminus. The 14-3-3 proteins have been implicated in the regulation of a wide range of biological processes (reviewed in Aitken et al. (1992) *Trends Biochem. Sci.* 17: 498). These proteins may function as regulators in signal transduction/phosphorylation mechanisms (Aitken et al. (1992) op.cit).

In mammals, the 14-3-3 proteins are a family of acidic proteins, certain members of which are present mainly in the brain and have a role in monoamine synthesis based on their ability to activate tyrosine and tryptophan hydroxylases in the presence of type II Ca2+/calmodulin-dependent protein kinase. For example, some 14-3-3 proteins activate protein kinase C at about 2-fold more than the known level of the activated protein kinase, i.e. the activity of protein kinase C in the presence of Ca2+ and phospholipids. This indicates that the cellular activity of protein kinase C can be regulated by diverse members of the 14-3-3 family. For example, quantitative analysis indicates that the tissue distribution of bovine brain 14-3-3 protein is more closely related to the known distributions of the Ca2(+)-dependent protein kinases, i.e., Ca2+/calmodulin- and Ca2+/phospholipid-dependent protein kinases, rather than those of tyrosine and tryptophan hydroxylases. This result, together with other available data on this protein, indicates roles of the 14-3-3 protein in more diverse kinase-mediated processes than the predicted role in monoamine synthesis. The 14-3-3 protein family appears to function, at least in part, as a multifunctional regulator of cell signalling processes mediated by two types of Ca(2+)-dependent protein kinase, protein kinase C and type II calmodulin-dependent protein kinase. Various functions have been reported for members of the 14-3-3 family, including phospholipase A2 activity and regulation of tyrosine hydroxylase, tryptophan hydroxylase, protein kinase C activities, and the activation of an exogenous ADP-ribosyltransferase (Fu et al. (1993) *Proc. Natl. Acad. Sci.* (USA) 90: 2320).

Many members of the 14-3-3 protein family have no known function. However, indicative evidence of functional properties has been identified for some 14-3-3 homologs.

Zupan et al. (1992) op.cit. cloned and expressed the human equivalent of a 30 Kd isoform of the major phospholipase A2 of sheep platelets and demonstrated that it catalyzes the cleavage of the sn-2 fatty acid of choline and ethanolamine glycerophospholipids. The 30-kDa polypeptide is over 50-fold selective for arachidonic acid and is augmented by calcium ion. Sequence homology analysis demonstrated that the 30 kD polypeptide is a member of the 14-3-3- family of proteins. This human 14-3-3 intracellular phospholipase appears to participate in arachidonic acid metabolism in endogenous phospholipid storage depots.

Leffers et al. (1993) op.cit. have identified a family of abundant acidic human keratinocyte proteins with apparent molecular masses ranging between 30,000 and 31,100 that share peptide sequences with each other, with protein 14-3-3, and with the kinase C inhibitory protein. The cloned and sequenced members of this family indicated that one cDNA coded for stratifin, and other clones (clones 1054, HS1 and AS1) were identified by structural comparison to sequence databases. Database searches indicated that clone HS1 corresponds to a human T-cell cDNA 14-3-3 clone, while a high level of similarity of clones 1054 and AS1 with the 14-3-3 beta and eta isoform sequences respectively, indicated that they code for the human equivalent of the two bovine proteins. Thus, HS1 1054 may be referred to as 14-3-3β.

The BMH1 gene from the yeast *Saccharomyces cerevisiae* encodes a putative protein which is more than 65% identical with mammalian 14-3-3 (the bovine brain 14-3-3 protein and proteins isolated from sheep brain which are strong inhibitors of protein kinase C). Disruption mutants and strains with the BMH1 gene on multicopy plasmids have impaired growth on minimal medium with glucose as carbon source, indicating a growth regulatory function of the bmh1 protein (van Heusden et al. (1992) op.cit.). A second gene, BMH-2, has been identified, and homozygous disruption of this gene is lethal.

A full-length complementary DNA clone from a normal human mammary epithelial cell encoding a 25-kilodalton protein, HME1, was isolated and found to be expressed primarily in epithelial cells. The HME1 sequence has extensive sequence homology with bovine 14-3-3 protein, however the tissue distribution, arrangement of charged amino acids, and location of potential phosphorylation sites of HME1 differ from those of 14-3-3. Compared with normal mammary epithelial cells, expression of HME1 mRNA was low in two cell lines derived from human mammary carcinoma and in a line of normal mammary epithelial cells transformed by oncogenes. HME1 therefore appears to be a cellular differentiation marker that may be down-regulated during neoplastic transformation. (Prasad et al. (1992) op.cit.).

Thus, members of the 14-3-3 protein family are evidently involved in cell growth control and are implicated in neoplasia, and may be involved in controlling apoptosis, acting as tumor suppressor gene products, participating in signal transduction pathways, and the like.

It is an object of the invention to provide a mechanistic coupling between various cell cycle control and signal transduction pathways by which aberrant cell growth and/or differentiation and/or apoptosis is effected. Such a coupling provides methods for screening agents which modulate cell cycle control and signal transduction, compositions comprising novel blocking agents for inhibiting interaction between components of such pathways, and therapeutic approaches to treating or preventing pathological conditions that result, at least in part, from aberrant cell cycle control, cell differentiation, and/or apoptosis.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference.

SUMMARY OF THE INVENTION

A basis of the present invention is the unexpected finding that certain human 14-3-3 proteins bind to raf-1 protein intracellularly as determined by a two-hybrid assay system. Prior to the present invention, this finding was not known or predictable and provides a basis for drug development screening assays, therapeutic methods for treating disease, and novel compositions of agents capable of modulating the binding interaction between one or more of the 14-3-3 protein species which bind to raf-1 protein.

The present invention provides compositions and methods for screening for agents which are modulators of raf-1 function and can modulate raf-1-mediated cell cycle control and/or modulate neoplastic and other pathological conditions dependent upon raf-1 functional interaction with 14-3-3 proteins.

The present invention provides a composition comprising a substantially pure protein complex comprising a raf-1 polypeptide and a 14-3-3 polypeptide. The invention also provides fragments of raf-1 and 14-3-3 polypeptides which retain the ability to bind, forming a raf-1:14-3-3 complex under physiological conditions. In one variation, the raf-1 polypeptide comprises the amino-terminal 197 amino acids of human raf-1 (aa1-aa197; numbering convention relative to full-length human raf-1 protein shown in FIG. 1A-1-1F is SEQ ID NO. 1; aa1-aa197 is SEQ ID NO. 2), which contain CR1 (conserved region 1). In a variation, the raf-1 polypeptide comprises the amino acids comprising CR2 (conserved region 2) of human raf-1, such as a fragment containing aa186-aa332 of human raf-1 (SEQ ID NO. 3). In one embodiment, the raf-1 polypeptide comprises the region of CR1 containing the protein kinase C (PK-C) homologous zinc finger domain. In a variation, the raf-1 polypeptide lacks approximately aa51-aa131 (optionally also lacking aa1-aa50) and comprises the conserved cysteine residues of the zinc finger motif. In one example, the raf-1 polypeptide is a full-length human raf-1 protein, however other mammalian raf-1 homolog polypeptides can be substituted.

In one embodiment, the 14-3-3 polypeptide comprises a human HS1 1054 ("14-3-3β") polypeptide (Leffers et al. (1993) op.cit), such as the polypeptide sequence of FIG. 2 panel B (SEQ ID NO 4), or a fragment or analog thereof having the property of binding to raf-1 in a yeast two-hybrid functional complementation assay.

In one embodiment, the 14-3-3 polypeptide comprises a human polypeptide described by Zupan et al. (1993) op.cit as an intracellular phospholipase and identified herein as "P1A2" or "14-3-3ζ". Such a polypeptide sequence as FIG. 3B (SEQ ID NO. 5) or a fragment or analog thereof having the property of binding to raf-1 in a yeast two-hybrid functional complementation assay can be used.

In one variation, other 14-3-3 protein family members (i.e., having a polypeptide segment of at least 20 amino acids which is substantially identical (see Definitions, infra) to the bovine brain 14-3-3 protein or fragments thereof which bind raf-1 can be employed as raf-1 binding partners.

In one aspect, the present invention provides substantially purified fragments of raf-1 and/or HS1 1054 and/or P1A2 protein(s). Typically, such polypeptide fragments comprise a binding interface, i.e., a portion sufficient to provide functional complementation in a yeast two-hybrid system, wherein the hybrid comprising the first binding interface (raf-1) is allowed to bind to a hybrid containing the second binding interface (14-3-3; HS1 1054 or P1A2). Such binding interfaces may comprise more than 15 amino acids, typically more than 25 amino acids, generally more than 40 amino acids, often more than 60 amino acids to 100 amino acids or more; the binding interfaces can be less than a full-length raf-1 or 14-3-3 protein, usually less than 100 amino acids, frequently less than 50 amino acids, and may contain fewer than 25–35 amino acids or less.

In one aspect, the present invention provides peptidomimetic compounds which comprise structural features of a raf-1 or 14-3-3 binding interface, such that the peptidomimetic is an agonist, partial agonist, or antagonist of functional binding of raf-1 to a 14-3-3 protein (e.g., HS1 1054 or P1A2).

The present invention provides several novel methods and compositions for modulating the activity of the raf-1 gene product and/or a 14-3-3 protein (e.g., HS1 1054 or P1A2) and thereby modulating cell proliferation, neoplasia, and cell differentiation. Generally, the methods comprise administering to a patient a therapeutically effective dose of an agent that modulates (e.g., inhibits) functional binding of raf-1 to a 14-3-3 protein. Such raf-1 modulating agents may comprise polynucleotides encoding fragments of raf-1 or a 14-3-3 protein, wherein such fragments typically comprise a binding interface or structural analog thereof. Such agents may comprise peptidomimetics of a raf-1 binding interface (i.e., the portion of raf-1 which mediates and/or is sufficient for binding to a 14-3-3 protein such as HS1 1054 or P1A2. Such agents may comprise peptidomimetics of a 14-3-3 binding interface (i.e., the portion of a 14-3-3 protein such as HS1 1054 or P1A2 which mediates and/or is sufficient for binding to raf-1. In some embodiments, the agent comprises a small molecule which may have or lack identifiable structural similarity to a binding interface.

Polynucleotide sequences encoding raf-1-interacting 14-3-3 polypeptides or encoding raf-1 polypeptides which have a binding interface for interacting with a 14-3-3 protein are provided. The characteristics of the cloned sequences are given, including the nucleotide and predicted amino acid sequences in FIG. 1A-1-3B. Polynucleotides comprising these sequences can serve as templates for the recombinant expression of quantities of raf-1-interacting polypeptides or 14-3-3 interacting polypeptides, such as human raf-1, human HS1 1054, or human P1A2, or binding interfaces thereof.

In one embodiment, candidate therapeutic agents are identified by their ability to block the binding of a raf-1interacting 14-3-3 polypeptide to a raf-1 polypeptide. The raf-1 polypeptide preferably is a full-length mature raf-1 protein, although fragments or analogs containing the 14-3-3 binding interface of raf-1 can be used. Typically, the raf-1 polypeptide comprises an amino acid sequence identical to a naturally-occurring raf-1 protein sequence, although mutant raf-1 polypeptides are sometimes used if the mutant raf-1 polypeptide binds to the raf-1-interacting polypeptide under control assay conditions (e.g., physiological conditions). Agents are tested for their ability to alter binding between a raf-1 polypeptide and a raf-1-interacting 14-3-3 polypeptide (e.g., human HS1 1054, human P1A2, or binding interfaces thereof) under suitable assay binding conditions. One means for detecting binding of a raf-1 polypeptide to a raf-1interacting 14-3-3 polypeptide is to immobilize the raf-1 polypeptide, such as by covalent or noncovalent chemical linkage to a solid support, and to contact the immobilized raf-1 polypeptide with a raf-1-interacting 14-3-3 polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a raf-1 polypeptide to a raf-1-interacting 14-3-3 polypeptide comprising a functional raf-1 binding interface. Binding of the labeled raf-1-interacting 14-3-3 polypeptide to the immobilized raf-1 is measured by determining the extent to which the labeled raf-1-interacting polypeptide is immobilized as a result of a specific binding interaction. Such specific binding may be reversible, or may be optionally irreversible if a cross-linking agent is added in appropriate experimental conditions. Alternatively, the raf-1 polypeptide may be labelled and the raf-1-interacting 14-3-3 polypeptide immobilized. In one variation, the binding assay is performed with soluble (i.e., non-immobilized) raf-1 and raf-1-binding 14-3-3 polypeptides and the resultant bound complexes (raf-1:raf-1-binding 14-3-3 polypeptide) are separated from unbound raf-1 and raf-1-binding polypeptides, and the bound complexes are quantitated. Agents that inhibit or augment the formation of bound complexes as compared to a control binding reaction lacking agent are thereby identified as raf-1-modulating agents and are candidate therapeutic agents.

In one variation, the binding assay is performed in vivo in a cell, such as a yeast cell (e.g., Saccharomyces), and agents which inhibit intermolecular binding between a raf-1 protein and a raf-1-interacting 14-3-3 polypeptide are identified as raf-1-modulating agents. Frequently, the in vivo screening assay is a yeast two-hybrid system wherein the yeast cells express: (1) a first fusion protein comprising raf-1 (or a 14-3-3 binding interface thereof) and a first transcriptional regulatory protein sequence (e.g., GAL4 activation domain), (2) a second fusion protein comprising a raf-1-interacting 14-3-3 polypeptide (or a raf-1 binding interface thereof) and a second transcriptional regulatory protein sequence (e.g., GAL4 DNA-binding domain), and (3) a reporter gene (e.g., β-galactosidase) which is transcribed when an intermolecular complex comprising the first fusion protein and the second fusion protein is formed. If a functional raf-1:raf-1-interacting 14-3-3 polypeptide complex forms, such as in a control assay lacking agent, the cell expresses the reporter gene which can be detected. Agents which inhibit or augment formation of functional raf-1:raf-1-interacting 14-3-3 polypeptide complexes (and thus reporter gene expression) are thereby identified as raf-1-modulating agents. Alternatively, the in vivo screening assay may be a yeast two-hybrid system wherein the yeast cells express: (1) a first fusion protein comprising raf-1 (or a 14-3-3 binding interface thereof) and a GAL4 DNA-binding domain, (2) a second fusion protein comprising a raf-1-interacting 14-3-3 polypeptide (or a raf-1 binding interface thereof) and a GAL4 transcription activator domain, and (3) a reporter gene (e.g., β-galactosidase) which is transcribed when an intermolecular complex comprising the first fusion protein and the second fusion protein is formed.

BRIEF DESCRIPTION OF THE FIGURES

FIGS. 1A-1-1E show the nucleotide sequence (SEQ. ID NO. 1) and deduced amino acid sequence (SEQ ID NO. 2)

of human raf-1. FIG. 1F shows the peptide sequences of full-length human Raf-1, (SEQ ID NO: 2) Raf-1 (aa1-aa197), (SEQ ID NO: 3), Raf-1 (aa186-aa332) (SEQ. ID NO: 4, Raf-1(aa303-aa648) (SEQ ID NO: 5).

FIG. 2 shows the nucleotide sequence (SEQ ID NO: 6) (panel A) and deduced amino acid sequence (SEQ ID NO. 7) (panel B) of human HS1 1054 (14-3-3β). Initiation and termination codons are capitalized.

FIG. 3A-1-3A-2 shows the nucleotide sequence of human P1A2 (14-3-3ζ) (SEQ. ID NO. 8) and FIG. 3B shows the deduced amino acid sequence of human P1A2 (14-3-3ζ). (SEQ ID NO: 9) Initiation and termination codons are capitalized.

FIG. 5 shows activation of Raf by 14-3-3 proteins in yeast. The Raf protein was affinity purified from solubilized P100 fractions from various derivatives described on page 44. An aliquot of each preparation was incubated with saturating amounts of recombinant MEK (8 μg) and $\gamma^{32}$P-ATP (5 μCi) for 20 minutes at 30° C. The reactions were stopped by addition of Laemelli buffer and boiled for 5 minutes. The phosphorylated products were separated by SDS-PAGE and quantitated with an AMBIS scanner. The counts incorporated into MEK were corrected for the amount of Raf proteins as measured by Western blotting. The relative Raf activity was normalized versus the basal level activity of the control. Vertical bars represent standard errors calculated on the means of three experiments.

DEFINITIONS

Figure 4:
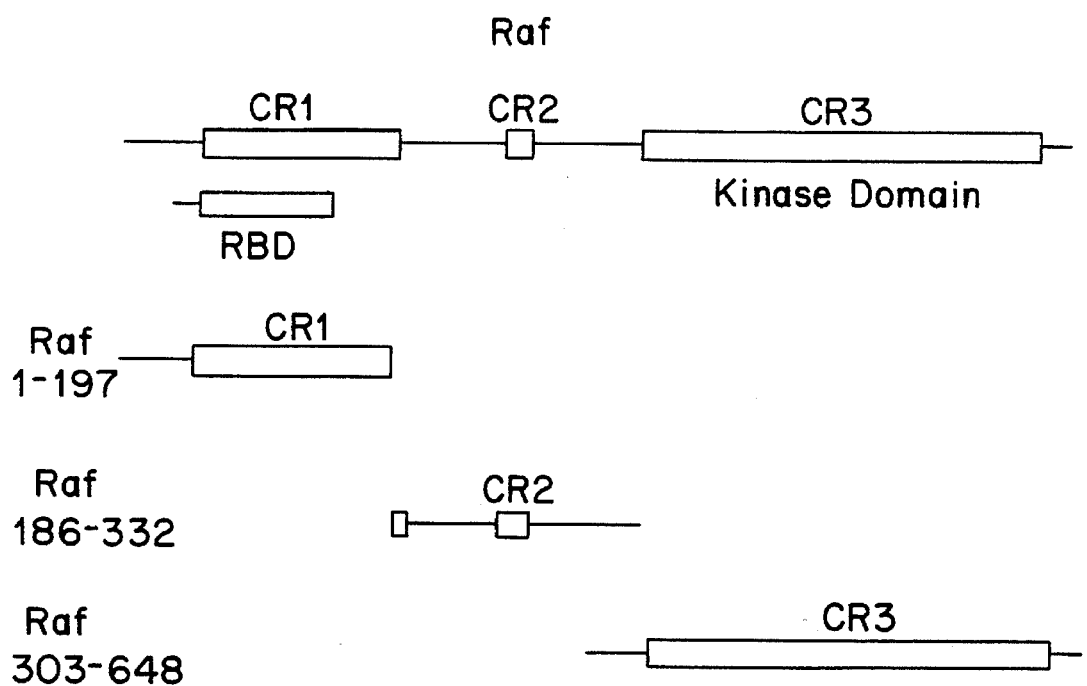
FIG. 4 shows the regions of human Raf kinase used for determining the region of interaction with 14-3-3 proteins. Raf(1-197) contains the RBD (aa51-aa131) and the zinc-finger-like region, which together constitute CR1. Raf(186-332) contains the CR2 domain. Raf(303-648) includes the entire kinase domain (CR3).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis*, 2nd Edition, E. S. Golub and D. R. Gren, Eds., Sinauer Associates, Sunderland, Mass. (1991), which is incorporated herein by reference). Stereoisomers (e.g., Damino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence" "comparison window" "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1A-1D-2 or FIG. 2A–2B, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the human raf-1 polynucleotide sequence shown in FIG. 1A-1-1E or the human HS1 1054 polynucleotide sequence shown in FIG. 2 (panel A).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatichydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion, but where the remaining amino acid sequence is identical to the corresponding positions in the naturally-occurring (e.g., mature protein) sequence deduced, for example, from a full-length cDNA sequence (e.g., the cDNA sequence shown in FIG. 1A-1-3B). Fragments typically are at least 14 amino acids long, preferably at least 20 amino acids long, usually at least 50 amino acids long or longer.

The term "analog" as used herein refers to polypeptides which are comprised of a segment of at least 15 amino acids that has substantial identity to a portion of the deduced amino acid sequence shown in FIG. 1A-1-3B and which has at least one of the following properties: (1) specific binding to a raf-1 polypeptide or 14-3-3 polypeptide (e.g., human raf-1 protein, human HS1 1054 or P1A2 protein) under suitable binding conditions, or (2) ability to modulate raf-1 activity when expressed in a mammalian cell. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring raf-1-interacting 14-3-3 polypeptide or raf-1 polypeptide (e.g., as shown in FIG. 1A-1-3B. Some raf-1-interacting 14-3-3 polypeptide analogs may lack biological activity but may still be employed for various uses, such as for raising antibodies to raf-1-interacting 14-3-3 polypeptide epitopes, as an immunological reagent to detect and/or purify α-raf-1-interacting 14-3-3 polypeptide antibodies by affinity chromatography, or as a competitive or noncompetitive agonist, antagonist, or partial agonist of native raf-1-interacting 14-3-3 polypeptide function.

The term "polypeptide" is used herein as a generic term to refer to native protein, fragments, or analogs of a polypeptide sequence. Hence, native protein, fragments, and analogs are species of the polypeptide genus. Preferred raf-1-interacting 14-3-3 polypeptides include: the human full=length protein comprising the polypeptide sequence shown in FIGS. 2B and 3B, or polypeptides comprising a raf-1 CR2 zinc finger, such as consisting essentially of a sequence shown in FIG. 1F.

The term "modulation of raf-1" is used herein to refer to the capacity to either enhance or inhibit a functional property of raf-1 (e.g., raf kinase activity, transcriptional enhancement activity, cell replication phenotype); such enhancement or inhibition may be contingent on the occurrence of a specific event, such as activation of a signal transduction pathway, and/or may be manifest only is particular cell types. The altered ability of raf-1 to modulate transcriptional enhancement or inhibition may affect the inducible transcription of a gene or gene subset, or may effect the basal level transcription of a gene, or both.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential activity as raf-1 modulatory agents (e.g., antineoplastic agents, cytotoxic agents, cell proliferation-promoting agents, and the like) by inclusion in screening assays described hereinbelow.

The term "candidate agent" is used herein to refer to an agent which is identified by one or more screening method(s) of the invention as a putative raf-1 modulatory agent or 14-3-3 modulatory agent. Some candidate modulatory agents may have therapeutic potential as drugs for human use.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

As used herein the terms "pathognomonic concentration" "pathognomonic amount" and "pathognomonic staining pattern" refer to a concentration, amount, or localization pattern, respectively, of a raf-1-interacting 14-3-3 polypeptide or mRNA in a sample, that indicates the presence of a disease condition or a predisposition to developing a disease, such as neoplasia or senescence. A pathognomonic amount is an amount of a raf-1-interacting 14-3-3 polypeptide or encoding mRNA in a cell or cellular sample that falls outside the range of normal clinical values that is established by prospective and/or retrospective statistical clinical studies. Generally, an individual having a disease (e.g., neoplasia) will exhibit an amount of a raf-interacting 14-3-3 polypeptide or mRNA in a cell or tissue sample that is significantly higher or lower than the range of concentrations that characterize normal, undiseased individuals; typically the pathognomonic concentration is at least about one standard deviation above or below the mean normal value, more usually it is at least about two standard deviations or more above or below the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Identification of raf-1-Interacting Polypeptide Sequences

Polypeptide sequences which interact with mammalian raf-1 polypeptide sequences may be identified by a variety of methods, including but not limited to: (1) co-immunoprecipitation of proteins associated with raf-1 in extracts of mammalian cells or cell nuclei, (2) screening of an expression library using a two-hybrid reporter system, such as a yeast two-hybrid system (Chien et al. (1991) *Proc. Natl. Acad. Sci.* (U.S.A.) 88: 9578; Zervos et al. (1993) *Cell* 72: 223), and (3) screening cDNA expression libraries with labeled raf-1 protein (or raf-1 protein which is subsequently detected with a labelled antibody) (Ayer et al. (1993) *Cell* 72: 211). Alternatively, an *E. coli*/BCCP interactive screening system (Germino et al. (1993) *Proc. Natl. Acad. Sci.* (U.S.A.) 90: 933; Guarente L (1993) *Proc. Natl. Acad. Sci.* (U.S.A.) 90: 1639, incorporated herein by reference) can be used to identify interacting protein sequences.

For proteins isolated by co-immunoprecipitation with raf-1 using and α-raf-1 antibody, generally the isolated raf-1-interacting polypeptide is purified to homogeneity and sequenced by Edman degradation. From the amino acid sequence(s) thus generated, degenerate oligonucleotide probes encoding the amino acid sequence(s) are produced and labelled for screening a cDNA or genomic library.

For polypeptide sequences identified by two-hybrid screening or cDNA library screening with raf-1 protein, the polynucleotide sequences encoding the raf-1-interacting polypeptide sequence are isolated and sequenced (e.g., by Sanger dideoxy sequencing), and the correct deduced amino acid sequence is determined.

For exemplification, the human HS1 1054 and P1A2 polynucleotide and deduced polypeptide sequences were isolated by screening a two-hybrid yeast expression system for polynucleotides encoding polypeptide sequences that bind to human a raf-1 fusion protein (see, Experimental Examples, infra).

Cloning of HS1 1054 and P1A2 Polynucleotides

Genomic or cDNA clones encoding HS1 1054 or P1A2 conveniently may be isolated from clone libraries (e.g., available from Clontech, Palo Alto, Calif.) using hybridization probes designed on the basis of the nucleotide sequences shown in FIGS. 2A and 3A-1-3A-2 and using conventional hybridization screening methods (e.g., Benton WD and Davis RW (1977) *Science* 196: 180; Goodspeed et al. (1989) Gene 76: 1; Dunn et al. (1989) *J. Biol. Chem.* 264: 13057). Where a cDNA clone is desired, clone libraries containing cDNA derived from cells expressing significant amounts of HS1 1054 or P1A2 mRNA is preferred. Alternatively, synthetic polynucleotide sequences corresponding to all or part of the sequences shown in FIG. 2A and 3A-1-3A-2 may be constructed by chemical synthesis of oligonucleotides. Additionally, polymerase chain reaction (PCR) using primers based on the sequence data disclosed in FIG. 2A and 3A-1-3A-2 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIGS. 2A and 3A-1-3A2 and a second primer that is not based on that sequence data may be used. For example, a second primer that is homologous to or complementary to a polyadenylation segment or randomer may be used.

It is apparent to one of skill in the art that nucleotide substitutions, deletions, and additions may be incorporated into the polynucleotides of the invention. Nucleotide sequence variation may result from sequence polymorphisms of various 14-3-3 (e.g., HS1 1054 or P1A2) or raf-1 alleles, minor sequencing errors, and the like. However, such nucleotide substitutions, deletions, and additions should not substantially disrupt the ability of the polynucleotide to hybridize to one of the polynucleotide sequences shown in FIG. 1A-1-3A-2 under hybridization conditions that are sufficiently stringent to result in specific hybridization.

Production of Polypeptides

The nucleotide and amino acid sequences shown in FIG. 1A-1-3B enable those of skill in the art to produce polypeptides corresponding to all or part of the full-length human raf-1, HS1 1054, or P1A2 polynucleotide or polypeptide sequences, respectively. Such polypeptides may be produced in prokaryotic or eukaryotic host cells by expression of polynucleotides encoding raf-1, HS1 1054, or P1A2, or fragments and analogs thereof, either alone or as part of a fusion protein (e.g. hybrid) or as an epitope-tagged variant. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume 152, Guide to Molecular Cloning Techniques* (1987), Academic Press, Inc., San Diego, Calif.

Fragments or analogs of raf-1, HS1 1054, or P1A2 may be prepared by those of skill in the art. Preferred amino- and carboxy-termini of fragments or analogs of raf-1, HS1 1054, or P1A2 (or other raf-1-interacting 14-3-3 protein) occur near boundaries of functional domains. For example, but not for limitation, such functional domains include: (1) domains conferring the property of binding to raf-1 (or a 14-3-3 protein), or (2) domains conferring the property of activating or suppressing raf-1 kinase activity when expressed at sufficient levels in cells expressing wild-type raf-1. Additionally, such functional domains might include domains having the capacity to directly alter local chromatin structure, which may comprise catalytic activities (e.g., topoisomerases, endonucleases) and/or which may comprise structural features (e.g., zinc fingers, histone-binding moieties), and domains which may interact with accessory proteins and/or transcription factors.

One method by which structural and functional domains may be identified is by comparison of the nucleotide and/or amino acid sequence data shown in FIG. 1A-1-3B to public or proprietary sequence databases. Preferably, computerized comparison methods are used to identify sequence motifs or predicted protein conformation domains that occur in other proteins of known structure and/or function, such as the zinc fingers. For example, the NAD-binding domains of dehydrogenases, particularly lactate dehydrogenase and malate dehydrogenase, are similar in conformation and have amino acid sequences that are detectably homologous (*Proteins, Structures and Molecular Principles,* (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the polypeptide sequences of the invention.

Additionally, computerized comparison of sequences shown in FIG. 1A-1-3B to existing sequence databases can identify sequence motifs and structural conformations found in other proteins or coding sequences that indicate similar domains of the raf-1 or 14-3-3 (HS1 1054 or P1A2) proteins. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a raf-1 or 14-3-3 sequence. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in raf-1 or 14-3-3 polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the raf-1 or 14-3-3 fragment. Alternatively, polypeptides wherein one or more functional domain have been deleted will exhibit a loss of the property normally conferred by the missing fragment.

Although one class of preferred embodiments are fragments having amino- and/or carboxy-termini corresponding to amino acid positions near functional domains borders, alternative fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations, but such fragments will typically comprise a functional binding interface.

In addition to fragments, analogs can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native raf-1 or 14-3-3 protein. However, raf-1, HS1 1054, or P1A2 analogs must comprise a segment of 25 amino acids that has substantial similarity to a portion of the amino acid sequence shown in FIG. 1A-1-3B, respectively, and which has at least one of the requisite functional properties enumerated (supra), typically a functional binding interface. Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs, possibly including interaction with raf-1. HS1 1054 or P1A2 analogs include various muteins of a HS1 1054 or P1A2 sequence other than the naturally-occurring peptide sequence. For example, single or multiple amino acid substitutions (preferably conservative amino acid substitutions) may be made in the naturally-occurring HS1 1054 or P1A2 sequence (preferably in the portion of the polypeptide outside the functional domains).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles,* (1984) Creighton (ed.), W. H. Freeman and Company, New York; *Introduction to Protein Structure,* (1991), C. Branden and J. Tooze, Garland Publishing, New York, N.Y.; and Thornton et al. (1991) *Nature* 354: 105; which are incorporated herein by reference).

Native raf-1 or 14-3-3 proteins, fragments thereof, or analogs thereof can be used as reagents in raf-1 binding assays for identifying agents that interfere with raf-1 function, said agents are thereby identified as raf-1 modulatory agents, which are candidate drugs. Typically, in vitro raf-1 binding assays that measure binding of a 14-3-3 polypeptide (e.g., HS1 1054 or P1A2) to raf-1. The 14-3-3 polypeptide is typically contacted with raf-1 polypeptide(s) under aqueous conditions that permit specific binding in control binding reactions with a binding affinity of about $1 \times 10^6$ $M^{-1}$ or greater (e.g., 10–250 mM NaCl or KCl and 5–100 mM Tris HCl pH 5–9, usually pH 6–8), generally may including $Zn^{+2}$ and/or $Mn^{+2}$ and/or $Mg^{+2}$ in the nanomolar to micromolar range (1 nM to 999 μM). Specificity of binding is typically established by adding unlabeled competitor at various concentrations selected at the discretion of the practitioner. Examples of unlabeled protein competitors include, but are not limited to, the following: unlabeled HS1 1054 or P1A2 polypeptide, bovine serum albumin, dry milk fractions, and nuclear protein extracts. Binding reactions wherein one or more agents are added are performed in parallel with a control binding reaction that does not include an agent. Agents which inhibit the specific binding of a 14-3-3 polypeptide to raf-1, as compared to a control reaction, are identified as candidate raf-1-modulatory drugs.

The nucleic acid sequences of the present invention capable of ultimately expressing the desired raf-1, HS1 1054, or P1A2 polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other Enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986) *Immunol. Rev.* 89: 49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papillomavirus, and the like. The vectors containing the DNA segments of interest (e.g., polypeptides encoding a raf-1 or 14-3-3 polypeptide) can be transferred into the host cell by well-known methods, which vary depending on the type of cellular host. For example, CaCl transfection is commonly utilized for prokaryotic cells, whereas $CaPO_4$ treatment or electroporation may be used for other cellular hosts. (See, generally, Maniatis, et al., *Molecular Cloning: A Laboratory Manual, Cold Spring Harbor Press,* (1982), which is incorporated herein by reference). Usually, vectors are episomes and are maintained extrachromosomally.

Expression of recombinant raf-1 or 14-3-3 protein in cells, may be used to identify and isolate genes that are transcriptionally modulated, either positively or negatively, by the presence of raf-1 and/or 14-3-3 protein (e.g., HS1 1054 or P1A2), either directly or via their interaction. Such genes are typically initially identified as cDNA clones isolated from subtractive cDNA libraries, wherein RNA isolated from cells expressing recombinant raf-1 and/or a raf-1-binding 14-3-3 protein, and RNA isolated from control cells (i.e., not expressing recombinant raf-1 and/or recombinant 14-3-3) are used to generate the subtractive libraries and screening probes. In such a manner, raf-1- and/or 14-3-3-dependent genes may be isolated. raf-1- or 14-3-3-dependent genes (or their regulatory sequences operably linked to a reporter gene) may be used as a component of an in vitro transcription assay.

Yeast Two-Hybrid Screening Assays

Yeast two-hybrid systems may be used to screen a mammalian (typically human) cDNA expression library, wherein cDNA is fused to a GAL4 DNA binding domain or activator domain, and a raf-1 or 14-3-3 polypeptide sequence is fused to a GAL4 activator domain or DNA binding domain, respectively. Such a yeast two-hybrid system can screen for cDNAs encoding proteins which bind to raf-1 or 14-3-3 sequences. For example, a cDNA library can be produced from mRNA from a human cell line or other suitable cell type. Such a cDNA library cloned in a yeast two-hybrid expression system (Chien et al. (1991) *Proc. Natl. Acad. Sci.* (U.S.A.) 88: 9578; Zervos et al. (1993) Cell 72: 233) can be used to identify cDNAs which encode proteins that interact with raf-1, HS1 1054, or P1A2 and thereby produce expression of the GAL4-dependent reporter gene. Polypeptides which interact with raf-1 or a 14-3-3 sequence can also be identified by immunoprecipitation of raf-1 or the 14-3-3 protein with specific antibody and identification of co-precipitating species. Further, polypeptides that bind raf-1, HS1 1054, or P1A2 or can be identified by screening a peptide library (e.g., a bacteriophage peptide display library, a spatially defined VLSIPS peptide array, and the like) with a raf-1 or the 14-3-3 polypeptide.

Methods for Rational Drug Design

HS1 1054 or P1A2 polypeptides, and other like 14-3-3 polypeptides, especially those portions which form direct contacts in raf-1: 14-3-3 complexes, can be used for rational drug design of candidate raf-1-modulating agents (e.g., antineoplastics and raf-1 modulators) and or can be used for design of 14-3-3-modulating agents. The substantially purified raf-1 or 14-3-3 protein and the identification of raf-1 as a docking partner for 14-3-3 proteins (e.g. HS1 1054 or P1A2), as provided herein permits production of substantially pure raf-1:HS1 1054 and raf-1:P1A2 polypeptide complexes (and raf-1 complexes with other 14-3-3 proteins) and computational models which can be used for protein X-ray crystallography or other structure analysis methods, such as the DOCK program (Kuntz et al. (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a raf-1:14-3-3 polypeptide complexes. Thus, the present invention may be used to design drugs, including drugs with a capacity to inhibit binding of raf-1 or a 14-3-3 protein (e.g., HS1 1054 or P1A2).

Thus, the present invention may be used to design drugs, including drugs with a capacity to inhibit binding of raf-1 to 14-3-3 proteins, such as HS1 1054 and P1A2.

The design of compounds that interact preferentially with a raf-1 or a 14-3-3 polypeptide or a raf-1:14-3-3 complex can be developed using computer analysis of three-dimensional structures. A set of molecular coordinates can be determined using: (1) crystallographic data, (2) data obtained by other physical methods, (3) data generated by computerized structure prediction programs operating on the deduced amino acid sequence data, or, preferably, a combination of these data. Examples of physical methods that may be used to define structure are, for example, two-dimensional homonuclear correlated spectroscopy (COSY). For those skilled in the art with one-dimensional NMR spectroscopy, COSY provides the kind of information available from a single-frequency decoupling experiment (e.g., which spins are scalar coupled to one another). In a COSY plot, the 1D spectrum lies along the diagonal, and the off-diagonal elements are present at the intersection of chemical shifts of groups that are J coupled. The "fingerprint" region contains ($^1H^N$, $1H^\alpha$) cross-peaks from the peptide backbone. The degree of resolution of the "fingerprint" region of the COSY map obtained in $H_2O$ is a good predictor of the success of sequence-specific assignments to be obtained without recourse to isotopic labeling.

Transferred nuclear Overhauser effect (TRNOE) spectra ($^1H$ NMR) relies on different 2D NOE spectra, and, in essence, looks at the conformation of the ligand just after it has dissociated from the protein. The use of TRNOE presumes, however, that the bound and free ligands are in fast exchange on the chemical shift time scale, which translates to a ligand $K_D$ greater than or equal to about $1\times10^{-4}$ M. TRNOE methods are useful to crosscheck and augment the distance information obtained by other approaches.

It is not intended that the present invention be limited by the particular method used to obtain structural information. Furthermore, it is not intended that the present invention be limited to a search for any one type of drug; one or more of the molecules may be naturally-occurring or may be synthetic, or may be a chemically-modified form of a naturally-occurring molecule.

In some embodiments, it is desirable to compare the structure of raf-1 or 14-3-3 protein(s) to the structure(s) of other proteins. This will aid in the identification of and selection of drugs that either selectively affect raf-1 or 14-3-3 proteins (or selectively affect a species of subcategory of 14-3-3 protein), or have a broad-spectrum effect on more than one species of related polypeptide (e.g., other raf-related proteins or other 14-3-3 proteins).

Methods of Identifying Novel raf-1-Modulating Agents

A basis of the present invention is the experimental finding that 14-3-3 proteins, such as HS1 1054 and P1A2, bind specifically to raf-1, a protein known to modulate cell proliferation in cells. For example, agents which block raf-1 function and/or block function of a 14-3-3 protein (e.g., HS1 1054 or P1A2) may be developed as potential human therapeutic drugs.

Candidate therapeutic agents are then tested further for antineoplastic activity or cell proliferation enhancement activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

raf-1:14-3-3 Intermolecular Binding

A basis of the present invention is the surprising finding that the raf-1 and 14-3-3 protein sequences form a complex under physiological conditions. This finding indicates that the 14-3-3 proteins, such as HS1 1054 and P1A2 serve as a modulators of raf-1 function, and vice versa. Such functional modulation can serve to couple a signal transduction pathway (via raf-1 or a 14-3-3 protein) to an cell proliferation regulatory protein.

Assays for detecting the ability of agents to inhibit the binding of raf-1 to a 14-3-3 protein such as HS1 1054 or P1A2 provide for facile high-throughput screening of agent banks (e.g., compound libraries, peptide libraries, and the like) to identify raf-1, HS1 1054, or P1A2 antagonists or agonists. Such antagonists and agonists may modulate raf-1, HS1 1054, or P1A2 activity and thereby modulate cell proliferation and neoplasia.

Administration of an efficacious dose of an agent capable of specifically inhibiting raf-1:HS1 1054 or raf1:P-1A2 complex formation (or raf-1:14-3-3 complex formation in general) to a patient can be used as a therapeutic or prophylactic method for treating pathological conditions (e.g., cancer, inflammation, proliferative diseases, autoimmune disease, and the like) which are effectively treated by modulating raf-1 and/or 14-3-3 protein function, such as HS1 1054 or P1A2 function and cell proliferation.

Binding assays generally take one of two forms: immobilized raf-1-interacting 14-3-3 polypeptide(s) can be used to bind labeled raf-1 polypeptide(s), or conversely, immobilized raf-1 polypeptide(s) can be used to bind labeled 14-3-3 polypeptides, wherein each polypeptide comprises a functional binding interface. Typically, a labeled 14-3-3 polypeptide (e.g., HS1 1054 or P1A2) is contacted with an immobilized raf-1 polypeptide under aqueous binding conditions and the extent of binding is determined by measuring the amount of immobilized labeled raf-1. In each case, the labeled polypeptide is contacted with the immobilized polypeptide under aqueous conditions that permit specific binding of the polypeptides(s) to form a raf-1:14-3-3 polypeptide complex in the absence of added agent. Particular aqueous conditions may be selected by the practitioner according to conventional methods. For general guidance, the following buffered aqueous conditions may be used: 10–250 mM NaCl, 5-50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of raf-1 to the 14-3-3 polypeptide(s) occurs in the control reaction(s). In some embodiments, where the assay detects formation of homodimers, modifications can be made to the basic binding reaction conditions so long as specific binding of a 14-3-3 polypeptide (e.g., HS1 1054 or P1A2) to a raf-1 polypeptide to form heterodimers occurs in the control reaction(s). Conditions that do not permit specific binding in control reactions (no agent included) are not suitable for use in binding assays.

Preferably, at least one polypeptide species is labeled with a detectable marker. Suitable labeling includes, but is not limited to, radiolabeling by incorporation of a radiolabeled amino acid (e.g., $^{14}C$-labeled leucine, $^{3}H$-labeled glycine, $^{35}S$-labeled methionine), radiolabeling by post-translational radioiodination with $^{125}I$ or $^{131}I$ (e.g., Bolton-Hunter reaction and chloramine T), labeling by post-translational phosphorylation with $^{32}P$ (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a 14-3-3 protein or raf-1 polypeptide may be used in combination with an accessory protein (e.g., a protein which forms a complex with the polypeptide in vivo), it is preferred that different labels are used for each polypeptide species, so that binding of individual and/or heterodimeric and/or multimeric complexes can be distinguished. For example but not limitation, a raf-1 or 14-3-3 polypeptide may be labeled with fluorescein and an accessory polypeptide may be labeled with a fluorescent marker that fluorescesces with either a different excitation wavelength or emission wavelength, or both. Alternatively, double-label scintillation counting may be used, wherein a raf-1 or 14-3-3 polypeptide is labeled with one isotope (e.g., $^{3}H$) and a second polypeptide species is labeled with a different isotope (e.g., $^{14}C$) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound raf-1:14-3-3 polypeptide complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles,* (1984) Creighton (ed.), W. H. Freeman and Company, New York).

Specific binding of labeled 14-3-3 polypeptide (e.g., HS1 1054 or P1A2) to immobilized raf-1 polypeptide, respectively, is determined by including unlabeled competitor protein(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a raf-1 or 14-3-3 polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci.* (U.S.A.) 83: 5889, which is incorporated herein by reference). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a raf-1-interacting 14-3-3 polypeptide to a raf-1 polypeptide, and/or to inhibit binding of 14-3-3 or raf-1 polypeptides to form homomultimers (homodimers).

Peptidomimetics of raf-1-Interacting Polypeptides

In addition to raf-1-interacting 14-3-3 polypeptides consisting only of naturally-occuring amino acids, HS1 1054 or P1A2 peptidomimetics are also provided, as are raf-1 peptidomimetics. Such peptidomimetics typically comprise structural features of a binding interface. Peptide analogs are commonly used in the pharmaceutical industry as nonpeptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) TINS p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human 14-3-3 protein having a raf-1 binding interface or a human raf-1 fragment comprising a 14-3-3 binding interface (e.g., the region of CR1 containing the PK-C-like zinc finger domain), but have one or more peptide linkages optionally replaced by a linkage selected from the group consisting of: $-CH_2NH-$, $-CH_2S-$, $-CH_2CH_2-$, $-CH=CH-$ (cis and trans), $-COCH_2-$, $-CH(OH)CH_2-$, and $CH_2SO-$, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 ($-CH_2NH-$, $CH_2CH_2-$); Spatola, A. F. et al., *Life Sci* (1986) 38:1243–1249 ($-CH_2-S$); Hann, M. M., *J Chem Soc Perkin Trans I* (1982) 307–314 ($-CH-CH-$, cis and trans); Almquist, R. G. et al., *J Med Chem* (1980) 23:1392–1398 ($-COCH_2-$); Jennings-White, C. et al., *Tetrahedron Lett* (1982) 23: 2533 ($-COCH_2-$); Szelke, M. et al., European Appln. EP 45665 (1982) CA: 97: 39405 (1982) ($-CH(OH)CH_2-$); Holladay, M. W. et al., *Tetrahedron Lett* (1983) 24: 4401–4404 ($-C(OH)CH_2-$); and Hruby, V. J., *Life Sci* (1982) 31: 189–199 ($-CH_2-S-$); each of which is incorporated herein by reference. A particularly preferred non-peptide linkage is $-CH_2NH-$. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., raf-1, 14-3-3) to which the peptidomimetic binds to produce the therapeutic effect. Derivitization (e.g., labelling) of peptidomimetics should not substantially interfere with the desired biological or pharmacological activity of the peptidomimetic. Peptidomimetics of raf-1 or 14-3-3 proteins may be used as competitive or noncompetitive agonists or antagonists of the 14-3-3 protein or raf-1 function, respectively. For example, a raf-1 peptidomimetic administered to a cell containing P1A2 protein and may compete with the naturally-occurring raf-1 protein and reduce P1A2 activity.

Systematic substitution of one or more amino acids of a consensus sequence with a D-amino acid of the same type (e.g., D-lysine in place of L-lysine) may be used to generate more stable peptides. In addition, constrained peptides (including cyclized peptides) comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide.

The amino acid sequences of raf-1, HS1 1054, and P1A2 polypeptides comprising binding interfaces identified herein will enable those of skill in the art to produce polypeptides corresponding to raf-1, HS1 1054, or P1A2 peptide sequences and sequence variants thereof having functional binding interfaces. Such polypeptides may be produced in prokaryotic or eukaryotic host cells by expression of polynucleotides encoding a raf-1, HS1 1054, or P1A2 polypeptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N. Y.; Berger and Kimmel, *Methods in Enzymology, Volume 152, Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al. (1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins,* Wiley Publishing, which are incorporated herein by reference).

Isolation of the Cognate Human Genes

The human HS1 1054 and P1A2 cDNA sequences are identified and genomic clones can be isolated by screening a human genomic clone library, such as a human genomic library in yeast artificial chromosomes, cosmids, or bacteriophage λ (e.g., λ Charon 35), with a polynucleotide probe comprising a sequence of about at least 30 contiguous nucleotides (or their complement) of the cDNA sequence shown in FIG. 2 panel A or FIG. 3A-1-3A-2, respectively. Typically, hybridization and washing conditions are performed at high stringency according to conventional hybridization procedures. Positive clones are isolated and sequenced. For illustration and not for limitation, a full-length polynucleotide corresponding to the sequence of FIG. 2A-3A-2 (panel A) or FIG. 3A may be labeled and used as a hybridization probe to isolate genomic clones from a human or murine genomic clone library in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5 x Denhardt's solution, 0.1–1% SDS, 100–200 μg sheared heterologous DNA or tRNA, 0–10% dextran sulfate, $1×10^5$ to $1×10^7$ cpm/ml of denatured probe with a specific activity of about $1×10^8$ cpm/μg, and incubation at 42° C. for about 6–36 hours. Prehybridization conditions are essentially identical except that probe is not included and incubation time is typically reduced. Washing conditions are typically 1–3 x SSC, 0.1–1% SDS, 50°–70° C. with change of wash solution at about 5–30 minutes.

Nonhuman cDNAs and genomic clones (i.e., cognate nonhuman HS1 1054 or P1A2 genes) can be analogously isolated from various nonhuman cDNA and genomic clone libraries available in the art (e.g., Clontech, Palo Alto, Calif.) by using probes based on the sequences shown in FIG. 2A-1-2B and FIG. 3A-1-3B, with hybridization and washing conditions typically being less stringent than for isolation of human clones.

Polynucleotides comprising sequences of approximately at least 30–50 nucleotides, preferably at least 100 nucleotides, corresponding to or complementary to the nucleotide sequences shown in FIG. 2A-3B can serve as PCR primers and/or hybridization probes for identifying and isolating germline genes corresponding to HS1 1054 or P1A2, respectively. These germline genes may be human or may be from a related mammalian species, preferably rodents or primates. Such germline genes may be isolated by various methods conventional in the art, including, but not limited to, by hybridization screening of genomic libraries in bacteriophage X or cosmid libraries, or by PCR amplification of genomic sequences using primers derived from the sequences shown in FIG. 2A-3B. Human genomic libraries are publicly available or may be constructed de novo from human DNA.

Genomic clones of HS1 1054 or P1A2, particularly of the murine cognate HS1 1054 or P1A2 gene, may be used to construct homologous targeting constructs for generating cells and transgenic nonhuman animals having at least one functionally disrupted HS1 1054 or P1A2 allele, preferably homozygous for knocked out HS1 1054 and/or P1A2 alleles. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated HS1 1054 or P1A2 allele. Such mice may be sold commercially as research animals for investigation of apoptosis, neoplasia, cell proliferation, signal transduction, drug screening, and other uses.

Chimeric targeted mice are derived according to Hogan, et al., *Manipulating the Mouse Embryo: A Laboratory Manual,* Cold Spring Harbor Laboratory (1988) and *Teratocarcinomas and Embryonic Stem Cells: A Practical Approach,* E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach,* E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a HS1 1054 or P1A2 cDNA or genomic gene copy may be used to construct transgenes for expressing HS1 1054 or P1A2 polypeptides at high levels and/or under the transcriptional control of transcription control sequences which do not naturally occur adjacent to the HS1 1054 or P1A2 gene. For example but not limitation, a constitutive promoter (e.g., a HSV-tk or pgk promoter) or a cell-lineage specific transcriptional regulatory sequence (e.g., an albumin, elastase, or CD4 or CD8 gene promoter/enhancer) may be operably linked to a HS1 1054- or P1A2-encoding polynucleotide sequence to form a transgene (typically in combination with a selectable marker such as a neo gene expression cassette). Such transgenes can be introduced into cells (e.g., ES cells, hematopoietic stem cells, cultured primary hepatocytes) and transgenic cells and transgenic nonhuman animals may be obtained according to conventional methods. Transgenic cells and/or transgenic nonhuman animals may be used to screen for antineoplastic agents and/or to screen for potential cell proliferation modulating agents, as overexpression of HS1 1054 or P1A2 or inappropriate expression of HS1 1054 or P1A2 may result in a hyperproliferative state or hypoproliferative state.

The following examples are offered by way of example and not by way of limitation. Variations and alternate embodiments will be apparent to those of skill in the art.

EXPERIMENTAL EXAMPLES

Background

Activation of the Map kinase pathway is a central event in the response of mammalian cells to mitogenic factors. Map kinase activation is essential for proliferation of fibroblasts in response to mitogenic growth factors, and in many cases is dependent on activated Ras. Raf-1 (Raf) protein kinase is a downstream effector of Ras, which in turn phosphorylates and activates MEK (Map kinase), the activator of Map kinases, ERK1 and ERK2.

Ras and Raf-1 interact directly both in vitro and in vivo, and this association is dependent on activated GTP-bound Ras and is mediated by the Ras effector domain and a region of Raf-1 containing part of its CR1 (conserved region 1) in the N-terminal regulatory domain of the protein. Activated Ras directs Raf kinase to the plasma membrane (13,14). Raf which was engineered to contain a CAAX box and is thereby directed to the plasma membrane becomes activated without the requirement for activated Ras (14). Ras is in this circumstance dispensable after membrane localization is achieved. However, the exact mechanism by which Raf becomes activated under most physiological circumstances has not yet been completely delineated in the art.

Overview

In order to identify protein sequences involved in the activation of Raf kinase, we performed a two-hybrid screen using a first fusion protein comprising a full-length human Raf-1 polypeptide sequence as the bait and a second fusion protein comprising a human polypeptide sequence encoded by a cDNA of a human cDNA library. We isolated two members of the 14-3-3 protein family (14-3-3β and 14-3-3ζ) which interact with N-terminal regulatory regions of the human Raf-1 protein and also display a weaker interaction with the C-terminal region (aa303-aa648) of Raf-1, but which do not compete with Ras for binding to Raf-1. 14-3-3 proteins associate with Raf-1 in mammalian cells and accompany Raf-1 to the membrane in the presence of activated Ras. When coexpressed with Raf-1 and MEK in yeast, mammalian 14-3-3β or 14-3-3ζ activates Raf-1 to a similar extent as does expression of Ras. Thus, 14-3-3 proteins participate in the regulation of Raf function.

Protein sequences which participate in Raf activation were identified using a two-hybrid screen (Fields et al. (1989) *Nature* 340: 245; Chien et al. (1991) op.cit.) of a HeLa cDNA library fused with the GAL4 activation domain was carried out, using full-length Raf protein kinase fused with GAL4 DNA-binding domain as the bait. Using this screening method, clones encoding two distinct members of the 14-3-3 protein family, designated 14-3-3β (human 1054; Leffers et al. (1993) *J. Mol. Biol.* 231: 982) and 14-3-3ζ (human P1A2; Fu et al. (1993) *Proc. Natl. Acad. Sci.* (USA). 90: 2320; Zupan et al. (1992) op.cit.) were identified.

To demonstrate the specificity of these interactions, the 14-3-3β and 14-3-3ζ protein fusions were tested for binding to APC$^{1034-2130}$ p53 Ras(Ser$^{186}$) and with GAL4 DNA-binding domain alone. No interaction between the 14-3-3β or 14-3-3ζ protein sequences and these control sequences was noted in the two-hybrid system. However, interaction between 14-3-3β and the bcr gene product, which itself has endogenous kinase activity, was detected.

To determine the region(s) of Raf which is involved in the interaction with 14-3-3 proteins, constructs encoding portions of Raf (FIG. 4) were cotransformed into yeast with either 14-3-3β or 14-3-3ζ, or with Ras(Ser186). The Ras(Ser$^{186}$) fusion interacted with full-length Raf and with the N-terminal region including CR1, but not with the middle region or C-terminal kinase domain. 14-3-3β and 14-3-3ζ interacted strongly with Raf(aa1-aa197), which contains the N-terminus and conserved region 1 (CR1). This region also contains the Ras-binding domain (aa51-aa131). 14-3-3β also interacted strongly with Raf(aa186-aa332), which contains the CR2 region, while the 14-3-3ζ interaction with this region was much weaker than that with Raf(aa1-aa197). Raf(aa303-aa648), which contains the kinase domain, also interacted with both 14-3-3 isoforms, although its interaction was weaker than was that of the other two portions of Raf. These data indicate that 14-3-3 proteins interact with at least two and likely three distinct regions of the Raf kinase. Thus, two or more separate regions of Raf are capable of associating with 14-3-3 proteins.

Since the 14-3-3 proteins interacted with the CR1 domain, it was possible that these 14-3-3 proteins interacted with the Ras-binding domain of Raf(aa51-aa131) and might compete for Ras binding. In an ELISA assay, recombinant 14-3-3β did not bind directly to the Ras-binding domain ("RBD") of Raf, nor did it compete with Ras for binding to the RBD. In agreement with two-hybrid results, we found no evidence for association between 14-3-3β and K-ras in the ELISA assay. These data indicate that the binding site on Raf for 14-3-3 proteins is distinct from the Ras-binding domain, and that Raf molecules bound to 14-3-3 protein may simultaneously be bound to Ras.

To determine if 14-3-3 proteins were associated with Raf in vivo, Raf was immunoprecipitated from Sf9 cells expressing catalytically inactive Raf, wildtype Raf, and wildtype Raf with v-src, and the resulting samples were Western blotted with antiserum reactive with 14-3-3 proteins. We observed 14-3-3 proteins in all of the Raf preparations. Preparations of unrelated proteins (H-sos, HPV E2) isolated from Sf9 cells did not contain detectable 14-3-3 proteins.

To determine if 14-3-3 proteins associate with Raf in mammalian cells, glu-glu-tagged Raf was expressed in COS cells, or coexpressed with 14-3-3β from transfected polynucleotides, and immunoprecipitated using anti-glu-glu Sepharose. The cells that expressed glu-glu-Raf yielded co-immunoprecipitated 14-3-3 proteins whether or not 14-3-3β was also co-expressed from a transfected polynucleotide. Lysates from cells which expressed 14-3-3β alone did not yield Raf or 14-3-3 proteins in the anti-glu-glu immunoprecipitates. Thus, Raf forms a complex with members of the 14-3-3 protein family in mammalian cells.

We investigated whether 14-3-3 proteins accompany Raf to the plasma membrane upon Ras activation. KT-3-tagged 14-3-3β was expressed in MDCK cells by microinjection of EXV expression plasmid and localized by immunofluorescence microscopy. When expressed alone or in combination with wildtype Raf, 14-3-3β localized in the cytosol and was not visible at the plasma membrane. In contrast, when the protein was expressed with activated Ras or with RafCAAX, we observed a partial but significant localization of 14-3-3β at the plasma membrane.

We also addressed the localization of 14-3-3 in COS cells by immunoprecipitation of Raf overexpressed alone or in combination with activated Ras. When Raf was expressed alone it was found almost exclusively in the S100 fraction and was accompanied by 14-3-3 protein. In contrast, a significant portion of Raf expressed with activated Ras was recovered in the P100 fraction and was also accompanied by 14-3-3 protein, again indicating that this protein accompanies Raf to the plasma membrane.

To address the functional consequences of the interaction between Raf and 14-3-3 proteins, we made use of a yeast system in which Raf activation is coupled to growth. In *Saccharomyces cerevisiae,* mating signals are transduced through a series of kinases which are homologous to the members of the Map kinase pathway in mammalian cells. They include Ste11, homologous to MEK kinase (Lange- Carter (1993) *Science* 260: 315), Ste7, which is the yeast MEK counterpart, and two Map kinases, Fus3 and Kss1 (Errede and Levin (1993) *Curr. Opin. Cell Biol.* 5: 254). One well established target of the Fus3 kinase is the Ste12 transcription factor known to promote transcription from promoters upstream of mating-inducible genes (Errede and Ammerer (1989) *Genes Devel.* 3: 1349). Fusion of one such promoter, that of the FUS1 gene, to the His3 gene renders the cells dependent on activation of the mating pheromone pathway for viability in the absence of exogenous histidine. We used a strain which is also mutated in one of the signalling components, the STE11 gene, and is therefore impaired for signalling and growth on his⁻ medium. This defect can be complemented by introduction of an active form of Raf, such as its constitutively active kinase domain, in conjunction with MEK. Full-length Raf does not signal in this system, but can be activated by overexpression of Ras. We chose this system to assess the ability of the 14-3-3 proteins to activate Raf in vivo. Introduction of the 14-3-3β and ζ genes into the ste11 mutant strain carrying full-length Raf integrated into the genome and the MEK gene on a plasmid resulted in stimulation of growth on his⁻ medium.

Strain SY1984R-L (MATα, ste11Δ, pep4Δ, his3Δ, FUS1::HIS3, leu2, ura3, trp1, can1, RAF::LEU2) was generated as follows: the Raf gene was subcloned downstream of the ADH promoter into the pADU vector, which is a high copy number yeast expression vector containing the selectable marker URA3, then a segment containing the promoter, the Raf gene, and the ADH terminator was introduced into the polylinker site of plasmid pRS405 (Stratagene) and the linearized plasmid was integrated at the LEU2 locus in the strain SY1984 (MATα, ste11Δ, pep4Δ his3Δ FUS1::HIS3 leu2 ura3 trp1 can1; available from K. Matsumoto, Dept. of Mol. Biol., Faculty of Science, Nagoya University, Nagoya, Japan) to generate the resultant strain SY1984R-L. Strain SY1984R-L was transformed with one of the following plasmids to generate the respective derivatives: the AAH5 vector (control), AAH-Ha-Ras (Ruggieri et al. (1992) *Mol. Cell. Biol.* 12: 758), AAH5-14-3-3β, and AAH5-14-3-3ζ. Four independent isolates of each derivative were plated on medium lacking histidine and growth was monitored for 3 days. This phenotype was strictly dependent on the presence of Ra# and MEK in the cell, indicating a specific effect on Raf. The degree of growth observed with the 14-3-3 clones was comparable to that obtained with Ras. FIG. 5 shows that Raf purified from cells expressing 14-3-3 proteins had a kinase activity that was 2–3 fold above background, as measured by its ability to phosphorylate recombinant MEK in vitro. This level of activation was sufficient for a biological stimulation of the pathway and was in the same range observed with Ras.

We have shown that Raf is present in mammalian cells in association with members of the 14-3-3 protein family. One region of Raf involved in the association with 14-3-3 proteins is the N-terminal portion containing CR1 and the Ras-binding domain (RBD). We have also shown that 14-3-3 proteins do not compete with Ras for binding to the RBD of Raf, and indicate that the region of Raf interaction with 14-3-3 proteins is outside the RBD. The 14-3-3 binding interaction with Raf likely involves the zinc-finger-like region of Raf just carboxy-terminal to the RBD, and likely includes the region of overlap between the CR1-containing clone and the Raf(186-332) clone.

Our observations indicate that Ras and 14-3-3 proteins (e.g., 14-3-3β and/or 14-3-3ζ) work together in a common pathway for Raf activation. Thus, identification of agents which modify the interaction(s) of 14-3-3 proteins with Raf can provide candidate drugs which control cell proliferation by modulating Raf activation.

Methods

Cloning of Raf-1 and subcloning for use in two-hybrid method:

The Raf-1 coding sequence was isolated by PCR amplification of a human placental cDNA library purchased from Stratagene (San Diego, Calif.) as described by MacDonald et al. (1993) *Mol. Cell Biol.* 13: 16.15. For use in the two hybrid screen (Chien et al. (1991) *Proc. Natl. Acad. Sci. USA* 88: 9578), the Raf-1 gene was fused to sequence encoding the GAL4-DNA binding domain by digesting pGEM Raf-I with NcoI and SacI to liberate the Raf-1 coding sequence and subcloning into the pGBT8 plasmid (Hannon et al. (1993) *Genes & Dev.* 7: 2378) digested also with Nco I and Sac I. Yeast (*S. cerevisiae*) of strain YGH-1 (Hannon et al. (1993) op.cit.) were transformed with pGBT8 Raf1, and the resultant strain was transformed with a HeLa cell cDNA library encoding fusions with the GAL4 activation domain in the plasmid pGAD (Chien et al. (1991) *Proc. Natl. Acad. Sci.* (USA) 88: 9578). The YGH-1 strain contains two reported genes, HIS3 and lacZ, which allow selection of cDNAs encoding proteins capable of interacting with the gene of interest, in this case, Raf-1. The first selection was by the ability to grow on plates lacking histidine. Positive colonies were then tested for production of β-galactodidase using X-gal as substrate as described by Hannon et al. op.cit. Of approximately 8×10⁶ transformants, 97 proved positive based on these two criteria. The pGAD plasmids from these 97 strains were then isolated and co-transformed into YGH-1 with the pGBT8 plasmid encoding GAL4-Raf-1 and, in parallel, with another pGBT8 plasmid encoding GAL4-DNA binding domain fused to a portion of the APC gene. Only ten of the 97 strains tested were specific in that they allowed growth on -His plates and production of β-galactosidase when co-expressed with the Ga14-Raf-1 fusion but not with the GAL4-APC fusion. Two of these 10 encoded the human gene for HS1 1054 (Leffers et al. (1993) *J. Mol. Biol.* 231: 982) and one encoded another member of the 14-3-3 family, which has been described as a phospholipase A₂ (Zupan et al. (1992) *J. Biol. Chem.* 267: 8707; Fu et al. (1993) *Proc. Natl. Acad. Sci. USA* 90: 2320). The sequences of HS1 1054 (14-3-3β) and P1A2 (14-3-3ζ) obtained by the two hybrid screen were full-length coding sequences for 14-3-3β and 14-3-3ζ, respectively. The HS1 1054 (14-3-3β) sequence obtained by the two hybrid system is substantially identical to as GenBank accession no. X57346, and the P1A2 (14-3-3ζ) sequence obtained by the two hybrid system is substantially identical to the GenBank sequence files referred to as accession nos. M86400 and L07955.

Cloning of Raf fragments for determining the region of interaction

We screened both of the 14-3-3 - GAL4 activation domain fusions in combination with plasmids encoding GAL4 DNA-binding domain fusions with three portions of the Raf-1 sequence. The first encodes Raf-1 amino acids 1 through 197. This was constructed as a PCR product using pGEM Raf as template and primers including restriction linkers for cloning into pGBT8 at Nco I and Sac I. This construct includes the N-terminus of the protein and the conserved region 1 (CR1). The second construct consists of Raf amino acids 186 through 332, which begins near the end of CR1 and includes conserved region 2 (CR2) and the entire middle portion of the protein up to the beginning of the kinase domain. This was similarly constructed as a PCR product using primers including restriction linkers also for NcoI and Sac I. The third construct consisted of Raf amino acids 303 through 648 (the C-terminus).

This construct codes for the entire kinase domain (CR3) as well as some surrounding sequence. It was made by inserting a PCR product coding for Raf-1 amino acids 303 through 381 into pGBT8-Raf-1 cut with Eco RI and Sal I.

Results in two hybrid using the constructs described above:

We found, using the constructs described above, that the 14-3-3 clones are able to associate with both the N-terminal CR1 portion and the middle region containing CR2. A weaker binding interaction between 14-3-3β and the C-terminal Raf portion comprising aa303-aa648 of human Raf and including the kinase domain was detected. The 14-3-3ζ bound even less strongly to the C-terminal portion (aa303-aa648).

The region of protein kinase C which associates with proteins of the 14-3-3 family is most likely the zinc finger-like region (Mochy-Rosen et al. (1992) *Biochemistry* 31: 8120) contained within aa1-aa197, and therefore, it seems likely that the region of CR1 containing the PK-C homologous zinc finger region of Raf-1 is responsible for binding to the 14-3-3 proteins as well. This region is N-terminal to the zinc finger region. Although there is an overlap of several amino acids between this N-terminal construct and the middle region construct, none of the conserved cysteine residues of the zinc finger motif are present in this middle region construct. Therefore, these data indicate that there are two distinct binding sites for the 14-3-3 proteins on the Raf-1 protein or that there is a complex binding pocket containing at least two regions of high enough affinity to be picked up in this two hybrid test.

Biological activity of 14-3-3 proteins on Raf expressed in yeast.

Strain SY1984 (MATs stella:: ura3 pep4::ura3 his3Δ200::ura3 FUS1::HIS3 leu2 ura3 trp1 can1) contains a readout gene, FUS1::HIS3, for the mating signal transduction pathway. This strain is therefore viable on media lacking histidine only if the pathway is activated. On the other hand, the ste11 mutation impairs the pathway. We have shown that the catalytic domain of Raf and the MEK protein can suppress this mutation and allow signaling through the pathway. In addition, full length Raf is inactive and requires activation, for example by H-ras, to signal. Effect of the 14-3-3 proteins on Raf We used the SY1984-R;L strain containing full length Raf and MEK to assess the ability of the 14-3-3 proteins to activate Raf and allow growth on histidine lacking (-his) media. The HS1 and the P1A2 clones were subcloned into plasmid pNV11 and introduced in the strain described above. Transformants containing these genes were tested for growth on -his media and showed to be positive. Biochemical analysis of Raf activity in cells containing the 14-3-3 proteins showed a two-fold increase over background.

Although the present invention has been described in some detail by way of illustration for purposes of clarity of understanding, it will be apparent that certain changes and modifications may be practiced within the scope of the claims.

We claim:

1. A composition comprising a substantially pure protein complex comprising a raf-1 polypeptide and a 14-3-3 polypeptide.

2. A composition of claim 1, wherein the protein complex comprises human raf-1 and the 14-3-3 polypeptide is human 14-3-3β or human 14-3-3ζ.

3. A composition of claim 1, wherein the raf-1 polypeptide comprises a zinc finger.

4. A composition of claim 1, wherein the raf-1 polypeptide comprises a CR1 or CR2 domain.

5. A composition comprising a protein complex comprising a raf-1 polypeptide and a 14-3-3 polypeptide, wherein said raf-1 polypeptide and 14-3-3 polypeptide are encoded by a heterologous polynucleotide expressed in a host cell.

6. A composition of claim 5, wherein the complex is present in a yeast cell.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2977 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 130..2076

( x i ) SEQUENCE DESCRIPTION: SEQ ID NO:1:

```
CCGAATGTGA CCGCCTCCCG CTCCCTCACC CGCCGCGGGG AGGAGGAGCG GGCGAGAAGC         60

TGCCGCCGAA CGACAGGACG TTGGGGCGGC CTGGCTCCCT CAGGTTTAAG AATTGTTTAA        120

GCTGCATCA ATG GAG CAC ATA CAG GGA GCT TGG AAG ACG ATC AGC AAT           168
          Met Glu His Ile Gln Gly Ala Trp Lys Thr Ile Ser Asn
            1               5                  10

GGT TTT GGA TTC AAA GAT GCC GTG TTT GAT GGC TCC AGC TGC ATC TCT          216
```

|  |  |  |  |  |  |  |  |  |  |  |  |  |  |  |  |
|---|---|---|---|---|---|---|---|---|---|---|---|---|---|---|---|
| Gly | Phe | Gly | Phe | Lys | Asp | Ala | Val | Phe | Asp | Gly | Ser | Ser | Cys | Ile | Ser |
|  | 15 |  |  |  | 20 |  |  |  |  | 25 |  |  |  |  |  |

| CCT | ACA | ATA | GTT | CAG | CAG | TTT | GGC | TAT | CAG | CGC | CGG | GCA | TCA | GAT | GAT | 264 |
|---|---|---|---|---|---|---|---|---|---|---|---|---|---|---|---|---|
| Pro | Thr | Ile | Val | Gln | Gln | Phe | Gly | Tyr | Gln | Arg | Arg | Ala | Ser | Asp | Asp |  |
| 30 |  |  |  |  | 35 |  |  |  |  | 40 |  |  |  |  | 45 |  |

| GGC | AAA | CTC | ACA | GAT | CCT | TCT | AAG | ACA | AGC | AAC | ACT | ATC | CGT | GTT | TTC | 312 |
|---|---|---|---|---|---|---|---|---|---|---|---|---|---|---|---|---|
| Gly | Lys | Leu | Thr | Asp | Pro | Ser | Lys | Thr | Ser | Asn | Thr | Ile | Arg | Val | Phe |  |
|  |  |  |  | 50 |  |  |  |  | 55 |  |  |  |  | 60 |  |  |

| TTG | CCG | AAC | AAG | CAA | AGA | ACA | GTG | GTC | AAT | GTG | CGA | AAT | GGA | ATG | AGC | 360 |
|---|---|---|---|---|---|---|---|---|---|---|---|---|---|---|---|---|
| Leu | Pro | Asn | Lys | Gln | Arg | Thr | Val | Val | Asn | Val | Arg | Asn | Gly | Met | Ser |  |
|  |  |  | 65 |  |  |  |  | 70 |  |  |  |  | 75 |  |  |  |

| TTG | CAT | GAC | TGC | CTT | ATG | AAA | GCA | CTC | AAG | GTG | AGG | GGC | CTG | CAA | CCA | 408 |
|---|---|---|---|---|---|---|---|---|---|---|---|---|---|---|---|---|
| Leu | His | Asp | Cys | Leu | Met | Lys | Ala | Leu | Lys | Val | Arg | Gly | Leu | Gln | Pro |  |
|  |  | 80 |  |  |  |  | 85 |  |  |  |  | 90 |  |  |  |  |

| GAG | TGC | TGT | GCA | GTG | TTC | AGA | CTT | CTC | CAC | GAA | CAC | AAA | GGT | AAA | AAA | 456 |
|---|---|---|---|---|---|---|---|---|---|---|---|---|---|---|---|---|
| Glu | Cys | Cys | Ala | Val | Phe | Arg | Leu | Leu | His | Glu | His | Lys | Gly | Lys | Lys |  |
|  | 95 |  |  |  |  | 100 |  |  |  |  | 105 |  |  |  |  |  |

| GCA | CGC | TTA | GAT | TGG | AAT | ACT | GAT | GCT | GCG | TCT | TTG | ATT | GGA | GAA | GAA | 504 |
|---|---|---|---|---|---|---|---|---|---|---|---|---|---|---|---|---|
| Ala | Arg | Leu | Asp | Trp | Asn | Thr | Asp | Ala | Ala | Ser | Leu | Ile | Gly | Glu | Glu |  |
| 110 |  |  |  |  | 115 |  |  |  |  | 120 |  |  |  |  | 125 |  |

| CTT | CAA | GTA | GAT | TTC | CTG | GAT | CAT | GTT | CCC | CTC | ACA | ACA | CAC | AAC | TTT | 552 |
|---|---|---|---|---|---|---|---|---|---|---|---|---|---|---|---|---|
| Leu | Gln | Val | Asp | Phe | Leu | Asp | His | Val | Pro | Leu | Thr | Thr | His | Asn | Phe |  |
|  |  |  |  | 130 |  |  |  |  | 135 |  |  |  |  | 140 |  |  |

| GCT | CGG | AAG | ACG | TTC | CTG | AAG | CTT | GCC | TTC | TGT | GAC | ATC | TGT | CAG | AAA | 600 |
|---|---|---|---|---|---|---|---|---|---|---|---|---|---|---|---|---|
| Ala | Arg | Lys | Thr | Phe | Leu | Lys | Leu | Ala | Phe | Cys | Asp | Ile | Cys | Gln | Lys |  |
|  |  |  | 145 |  |  |  |  | 150 |  |  |  |  | 155 |  |  |  |

| TTC | CTG | CTC | AAT | GGA | TTT | CGA | TGT | CAG | ACT | TGT | GGC | TAC | AAA | TTT | CAT | 648 |
|---|---|---|---|---|---|---|---|---|---|---|---|---|---|---|---|---|
| Phe | Leu | Leu | Asn | Gly | Phe | Arg | Cys | Gln | Thr | Cys | Gly | Tyr | Lys | Phe | His |  |
|  |  | 160 |  |  |  |  | 165 |  |  |  |  | 170 |  |  |  |  |

| GAG | CAC | TGT | AGC | ACC | AAA | GTA | CCT | ACT | ATG | TGT | GTG | GAC | TGG | AGT | AAC | 696 |
|---|---|---|---|---|---|---|---|---|---|---|---|---|---|---|---|---|
| Glu | His | Cys | Ser | Thr | Lys | Val | Pro | Thr | Met | Cys | Val | Asp | Trp | Ser | Asn |  |
|  | 175 |  |  |  |  | 180 |  |  |  |  | 185 |  |  |  |  |  |

| ATC | AGA | CAA | CTC | TTA | TTG | TTT | CCA | AAT | TCC | ACT | ATT | GGT | GAT | AGT | GGA | 744 |
|---|---|---|---|---|---|---|---|---|---|---|---|---|---|---|---|---|
| Ile | Arg | Gln | Leu | Leu | Leu | Phe | Pro | Asn | Ser | Thr | Ile | Gly | Asp | Ser | Gly |  |
| 190 |  |  |  |  | 195 |  |  |  |  | 200 |  |  |  |  | 205 |  |

| GTC | CCA | GCA | CTA | CCT | TCT | TTG | ACT | ATG | CGT | CGT | ATG | CGA | GAG | TCT | GTT | 792 |
|---|---|---|---|---|---|---|---|---|---|---|---|---|---|---|---|---|
| Val | Pro | Ala | Leu | Pro | Ser | Leu | Thr | Met | Arg | Arg | Met | Arg | Glu | Ser | Val |  |
|  |  |  |  | 210 |  |  |  |  | 215 |  |  |  |  | 220 |  |  |

| TCC | AGG | ATG | CCT | GTT | AGT | TCT | CAG | CAC | AGA | TAT | TCT | ACA | CCT | CAC | GCC | 840 |
|---|---|---|---|---|---|---|---|---|---|---|---|---|---|---|---|---|
| Ser | Arg | Met | Pro | Val | Ser | Ser | Gln | His | Arg | Tyr | Ser | Thr | Pro | His | Ala |  |
|  |  |  | 225 |  |  |  |  | 230 |  |  |  |  | 235 |  |  |  |

| TTC | ACC | TTT | AAC | ACC | TCC | AGT | CCC | TCA | TCT | GAA | GGT | TCC | CTC | TCC | CAG | 888 |
|---|---|---|---|---|---|---|---|---|---|---|---|---|---|---|---|---|
| Phe | Thr | Phe | Asn | Thr | Ser | Ser | Pro | Ser | Ser | Glu | Gly | Ser | Leu | Ser | Gln |  |
|  |  | 240 |  |  |  |  | 245 |  |  |  |  | 250 |  |  |  |  |

| AGG | CAG | AGG | TCG | ACA | TCC | ACA | CCT | AAT | GTC | CAC | ATG | GTC | AGC | ACC | ACG | 936 |
|---|---|---|---|---|---|---|---|---|---|---|---|---|---|---|---|---|
| Arg | Gln | Arg | Ser | Thr | Ser | Thr | Pro | Asn | Val | His | Met | Val | Ser | Thr | Thr |  |
| 255 |  |  |  |  | 260 |  |  |  |  | 265 |  |  |  |  |  |  |

| CTG | CCT | GTG | GAC | AGC | AGG | ATG | ATT | GAG | GAT | GCA | ATT | CGA | AGT | CAC | AGC | 984 |
|---|---|---|---|---|---|---|---|---|---|---|---|---|---|---|---|---|
| Leu | Pro | Val | Asp | Ser | Arg | Met | Ile | Glu | Asp | Ala | Ile | Arg | Ser | His | Ser |  |
| 270 |  |  |  |  | 275 |  |  |  |  | 280 |  |  |  |  | 285 |  |

| GAA | TCA | GCC | TCA | CCT | TCA | GCC | CTG | TCC | AGT | AGC | CCC | AAC | AAT | CTG | AGC | 1032 |
|---|---|---|---|---|---|---|---|---|---|---|---|---|---|---|---|---|
| Glu | Ser | Ala | Ser | Pro | Ser | Ala | Leu | Ser | Ser | Ser | Pro | Asn | Asn | Leu | Ser |  |
|  |  |  |  | 290 |  |  |  |  | 295 |  |  |  |  | 300 |  |  |

| CCA | ACA | GGC | TGG | TCA | CAG | CCG | AAA | ACC | CCC | GTG | CCA | GCA | CAA | AGA | GAG | 1080 |
|---|---|---|---|---|---|---|---|---|---|---|---|---|---|---|---|---|
| Pro | Thr | Gly | Trp | Ser | Gln | Pro | Lys | Thr | Pro | Val | Pro | Ala | Gln | Arg | Glu |  |
|  |  |  | 305 |  |  |  |  | 310 |  |  |  |  | 315 |  |  |  |

| CGG | GCA | CCA | GTA | TCT | GGG | ACC | CAG | GAG | AAA | AAC | AAA | ATT | AGG | CCT | CGT | 1128 |
|---|---|---|---|---|---|---|---|---|---|---|---|---|---|---|---|---|
| Arg | Ala | Pro | Val | Ser | Gly | Thr | Gln | Glu | Lys | Asn | Lys | Ile | Arg | Pro | Arg |  |
| 320 |  |  |  |  | 325 |  |  |  |  | 330 |  |  |  |  |  |  |

| GGA | CAG | AGA | GAT | TCA | AGC | TAT | TAT | TGG | GAA | ATA | GAA | GCC | AGT | GAA | GTG | 1176 |

| | | | | | | | | | | | | | | | | |
|---|---|---|---|---|---|---|---|---|---|---|---|---|---|---|---|---|
| | Gly | Gln | Arg | Asp | Ser | Ser | Tyr | Tyr | Trp | Glu | Ile | Glu | Ala | Ser | Glu | Val |
| | | 335 | | | | | 340 | | | | 345 | | | | | |

| ATG | CTG | TCC | ACT | CGG | ATT | GGG | TCA | GGC | TCT | TTT | GGA | ACT | GTT | TAT | AAG | 1224 |
|---|---|---|---|---|---|---|---|---|---|---|---|---|---|---|---|---|
| Met | Leu | Ser | Thr | Arg | Ile | Gly | Ser | Gly | Ser | Phe | Gly | Thr | Val | Tyr | Lys | |
| 350 | | | | | 355 | | | | | 360 | | | | | 365 | |

| GGT | AAA | TGG | CAC | GGA | GAT | GTT | GCA | GTA | AAG | ATC | CTA | AAG | GTT | GTC | GAC | 1272 |
|---|---|---|---|---|---|---|---|---|---|---|---|---|---|---|---|---|
| Gly | Lys | Trp | His | Gly | Asp | Val | Ala | Val | Lys | Ile | Leu | Lys | Val | Val | Asp | |
| | | | | 370 | | | | | 375 | | | | | | 380 | |

| CCA | ACC | CCA | GAG | CAA | TTC | CAG | GCC | TTC | AGG | AAT | GAG | GTG | GCT | GTT | CTG | 1320 |
|---|---|---|---|---|---|---|---|---|---|---|---|---|---|---|---|---|
| Pro | Thr | Pro | Glu | Gln | Phe | Gln | Ala | Phe | Arg | Asn | Glu | Val | Ala | Val | Leu | |
| | | | 385 | | | | | 390 | | | | | 395 | | | |

| CGC | AAA | ACA | CGG | CAT | GTG | AAC | ATT | CTG | CTT | TTC | ATG | GGG | TAC | ATG | ACA | 1368 |
|---|---|---|---|---|---|---|---|---|---|---|---|---|---|---|---|---|
| Arg | Lys | Thr | Arg | His | Val | Asn | Ile | Leu | Leu | Phe | Met | Gly | Tyr | Met | Thr | |
| | | 400 | | | | | 405 | | | | | 410 | | | | |

| AAG | GAC | AAC | CTG | GCA | ATT | GTG | ACC | CAG | TGG | TGC | GAG | GGC | AGC | AGC | CTC | 1416 |
|---|---|---|---|---|---|---|---|---|---|---|---|---|---|---|---|---|
| Lys | Asp | Asn | Leu | Ala | Ile | Val | Thr | Gln | Trp | Cys | Glu | Gly | Ser | Ser | Leu | |
| | 415 | | | | | 420 | | | | | 425 | | | | | |

| TAC | AAA | CAC | CTG | CAT | GTC | CAG | GAG | ACC | AAG | TTT | CAG | ATG | TTC | CAG | CTA | 1464 |
|---|---|---|---|---|---|---|---|---|---|---|---|---|---|---|---|---|
| Tyr | Lys | His | Leu | His | Val | Gln | Glu | Thr | Lys | Phe | Gln | Met | Phe | Gln | Leu | |
| 430 | | | | | 435 | | | | | 440 | | | | | 445 | |

| ATT | GAC | ATT | GCC | CGG | CAG | ACG | GCT | CAG | GGA | ATG | GAC | TAT | TTG | CAT | GCA | 1512 |
|---|---|---|---|---|---|---|---|---|---|---|---|---|---|---|---|---|
| Ile | Asp | Ile | Ala | Arg | Gln | Thr | Ala | Gln | Gly | Met | Asp | Tyr | Leu | His | Ala | |
| | | | | 450 | | | | | 455 | | | | | | 460 | |

| AAG | AAC | ATC | ATC | CAT | AGA | GAC | ATG | AAA | TCC | AAC | AAT | ATA | TTT | CTC | CAT | 1560 |
|---|---|---|---|---|---|---|---|---|---|---|---|---|---|---|---|---|
| Lys | Asn | Ile | Ile | His | Arg | Asp | Met | Lys | Ser | Asn | Asn | Ile | Phe | Leu | His | |
| | | | 465 | | | | | 470 | | | | | 475 | | | |

| GAA | GGC | TTA | ACA | GTG | AAA | ATT | GGA | GAT | TTT | GGT | TTG | GCA | ACA | GTA | AAG | 1608 |
|---|---|---|---|---|---|---|---|---|---|---|---|---|---|---|---|---|
| Glu | Gly | Leu | Thr | Val | Lys | Ile | Gly | Asp | Phe | Gly | Leu | Ala | Thr | Val | Lys | |
| | | | 480 | | | | | 485 | | | | | 490 | | | |

| TCA | CGC | TGG | AGT | GGT | TCT | CAG | CAG | GTT | GAA | CAA | CCT | ACT | GGC | TCT | GTC | 1656 |
|---|---|---|---|---|---|---|---|---|---|---|---|---|---|---|---|---|
| Ser | Arg | Trp | Ser | Gly | Ser | Gln | Gln | Val | Glu | Gln | Pro | Thr | Gly | Ser | Val | |
| | 495 | | | | | 500 | | | | | 505 | | | | | |

| CTC | TGG | ATG | GCC | CCA | GAG | GTG | ATC | CGA | ATG | CAG | GAT | AAC | AAC | CCA | TTC | 1704 |
|---|---|---|---|---|---|---|---|---|---|---|---|---|---|---|---|---|
| Leu | Trp | Met | Ala | Pro | Glu | Val | Ile | Arg | Met | Gln | Asp | Asn | Asn | Pro | Phe | |
| 510 | | | | | 515 | | | | | 520 | | | | | 525 | |

| AGT | TTC | CAG | TCG | GAT | GTC | TAC | TCC | TAT | GGC | ATC | GTA | TTG | TAT | GAA | CTG | 1752 |
|---|---|---|---|---|---|---|---|---|---|---|---|---|---|---|---|---|
| Ser | Phe | Gln | Ser | Asp | Val | Tyr | Ser | Tyr | Gly | Ile | Val | Leu | Tyr | Glu | Leu | |
| | | | | 530 | | | | | 535 | | | | | | 540 | |

| ATG | ACG | GGG | GAG | CTT | CCT | TAT | TCT | CAC | ATC | AAC | AAC | CGA | GAT | CAG | ATC | 1800 |
|---|---|---|---|---|---|---|---|---|---|---|---|---|---|---|---|---|
| Met | Thr | Gly | Glu | Leu | Pro | Tyr | Ser | His | Ile | Asn | Asn | Arg | Asp | Gln | Ile | |
| | | | 545 | | | | | 550 | | | | | 555 | | | |

| ATC | TTC | ATG | GTG | GGC | CGA | GGA | TAT | GCC | TCC | CCA | GAT | CTT | AGT | AAG | CTA | 1848 |
|---|---|---|---|---|---|---|---|---|---|---|---|---|---|---|---|---|
| Ile | Phe | Met | Val | Gly | Arg | Gly | Tyr | Ala | Ser | Pro | Asp | Leu | Ser | Lys | Leu | |
| | | 560 | | | | | 565 | | | | | 570 | | | | |

| TAT | AAG | AAC | TGC | CCC | AAA | GCA | ATG | AAG | AGG | CTG | GTA | GCT | GAC | TGT | GTG | 1896 |
|---|---|---|---|---|---|---|---|---|---|---|---|---|---|---|---|---|
| Tyr | Lys | Asn | Cys | Pro | Lys | Ala | Met | Lys | Arg | Leu | Val | Ala | Asp | Cys | Val | |
| 575 | | | | | 580 | | | | | 585 | | | | | | |

| AAG | AAA | GTA | AAG | GAA | GAG | AGG | CCT | CTT | TTT | CCC | CAG | ATC | CTG | TCT | TCC | 1944 |
|---|---|---|---|---|---|---|---|---|---|---|---|---|---|---|---|---|
| Lys | Lys | Val | Lys | Glu | Glu | Arg | Pro | Leu | Phe | Pro | Gln | Ile | Leu | Ser | Ser | |
| 590 | | | | | 595 | | | | | 600 | | | | | 605 | |

| ATT | GAG | CTG | CTC | CAA | CAC | TCT | CTA | CCG | AAG | ATC | AAC | CGG | AGC | GCT | TCC | 1992 |
|---|---|---|---|---|---|---|---|---|---|---|---|---|---|---|---|---|
| Ile | Glu | Leu | Leu | Gln | His | Ser | Leu | Pro | Lys | Ile | Asn | Arg | Ser | Ala | Ser | |
| | | | | 610 | | | | | 615 | | | | | 620 | | |

| GAG | CCA | TCC | TTG | CAT | CGG | GCA | GCC | CAC | ACT | GAG | GAT | ATC | AAT | GCT | TGC | 2040 |
|---|---|---|---|---|---|---|---|---|---|---|---|---|---|---|---|---|
| Glu | Pro | Ser | Leu | His | Arg | Ala | Ala | His | Thr | Glu | Asp | Ile | Asn | Ala | Cys | |
| | | | 625 | | | | | 630 | | | | | 635 | | | |

| ACG | CTG | ACC | ACG | TCC | CCG | AGG | CTG | CCT | GTC | TTC | TAGTTGACTT | TGCACCTGTC | 2093 |
|---|---|---|---|---|---|---|---|---|---|---|---|---|---|
| Thr | Leu | Thr | Thr | Ser | Pro | Arg | Leu | Pro | Val | Phe | | | |
| | | 640 | | | | | 645 | | | | | | |

TTCAGGCTGC CAGGGGAGGA GGAGAAGCCA GCAGGCACCA CTTTTCTGCT CCCTTTCTCC    2153

```
AGAGGCAGAA CACATGTTTT CAGAGAAGCT CTGCTAAGGA CCTTCTAGAC TGCTCACAGG      2213

GCCTTAACTT CATGTTGCCT TCTTTTCTAT CCCTTTGGGC CCTGGGAGAA GGAAGCCATT      2273

TGCAGTGCTG GTGTGTCCTG CTCCCTCCCC ACATTCCCCA TGCTCAAGGC CCAGCCTTCT      2333

GTAGATGCGC AAGTGGATGT TGATGGTAGT ACAAAAAGCA GGGGCCCAGC CCCAGCTGTT      2393

GGCTACATGA GTATTTAGAG GAAGTAAGGT AGCAGGCAGT CCAGCCCTGA TGTGGAGACA      2453

CATGGGATTT TGGAAATCAG CTTCTGGAGG AATGCATGTC ACAGGCGGGA CTTTCTTCAG      2513

AGAGTGGTGC AGCGCCAGAC ATTTTGCACA TAAGGCACCA ACAGCCCAG  GACTGCCGAG      2573

ACTCTGGCCG CCCGAAGGAG CCTGCTTTGG TACTATGGAA CTTTTCTTAG GGGACACGTC      2633

CTCCTTTCAC AGCTTCTAAG GTGTCCAGTG CATTGGGATG GTTTCCAGG  CAAGGCACTC      2693

GGCCAATCCG CATCTCAGCC CTCTCAGGAG CAGTCTTCCA TCATGCTGAA TTTTGTCTTC      2753

CAGGAGCTGC CCCTATGGGG CGGGCCGCAG GGCCAGCCTG TTTCTCTAAC AAACAAACAA      2813

ACAAACAGCC TTGTTTCTCT AGTCACATCA TGTGTATACA AGGAAGCCAG GAATACAGGT      2873

TTTCTTGATG ATTTGGGTTT TAATTTTGTT TTTATTGCAC CTGACAAAAT ACAGTTATCT      2933

GATGGTCCCT CAATTATGTT ATTTTAATAA AATAAATTAA ATTT                      2977
```

(2) INFORMATION FOR SEQ ID NO:2:

(i) SEQUENCE CHARACTERISTICS:
        (A) LENGTH: 648 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu His Ile Gln Gly Ala Trp Lys Thr Ile Ser Asn Gly Phe Gly
 1               5                  10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
        50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
               100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
                180                 185                 190

Leu Leu Leu Phe Pro Asn Ser Thr Ile Gly Asp Ser Gly Val Pro Ala
            195                 200                 205
```

-continued

| | | | | | | | | | | | | | | |
|---|---|---|---|---|---|---|---|---|---|---|---|---|---|---|
| Leu | Pro | Ser | Leu | Thr | Met | Arg | Arg | Met | Arg | Glu | Ser | Val | Ser | Arg | Met |
| | 210 | | | | | 215 | | | | 220 | | | | | |
| Pro | Val | Ser | Ser | Gln | His | Arg | Tyr | Ser | Thr | Pro | His | Ala | Phe | Thr | Phe |
| 225 | | | | | 230 | | | | | 235 | | | | | 240 |
| Asn | Thr | Ser | Ser | Pro | Ser | Ser | Glu | Gly | Ser | Leu | Ser | Gln | Arg | Gln | Arg |
| | | | | 245 | | | | | 250 | | | | | 255 | |
| Ser | Thr | Ser | Thr | Pro | Asn | Val | His | Met | Val | Ser | Thr | Thr | Leu | Pro | Val |
| | | | 260 | | | | | 265 | | | | | 270 | | |
| Asp | Ser | Arg | Met | Ile | Glu | Asp | Ala | Ile | Arg | Ser | His | Ser | Glu | Ser | Ala |
| | | 275 | | | | | 280 | | | | | 285 | | | |
| Ser | Pro | Ser | Ala | Leu | Ser | Ser | Ser | Pro | Asn | Asn | Leu | Ser | Pro | Thr | Gly |
| | 290 | | | | | 295 | | | | | 300 | | | | |
| Trp | Ser | Gln | Pro | Lys | Thr | Pro | Val | Pro | Ala | Gln | Arg | Glu | Arg | Ala | Pro |
| 305 | | | | | 310 | | | | | 315 | | | | | 320 |
| Val | Ser | Gly | Thr | Gln | Glu | Lys | Asn | Lys | Ile | Arg | Pro | Arg | Gly | Gln | Arg |
| | | | | 325 | | | | | 330 | | | | | 335 | |
| Asp | Ser | Ser | Tyr | Tyr | Trp | Glu | Ile | Glu | Ala | Ser | Glu | Val | Met | Leu | Ser |
| | | | 340 | | | | | 345 | | | | | 350 | | |
| Thr | Arg | Ile | Gly | Ser | Gly | Ser | Phe | Gly | Thr | Val | Tyr | Lys | Gly | Lys | Trp |
| | | 355 | | | | | 360 | | | | | 365 | | | |
| His | Gly | Asp | Val | Ala | Val | Lys | Ile | Leu | Lys | Val | Val | Asp | Pro | Thr | Pro |
| | 370 | | | | | 375 | | | | | 380 | | | | |
| Glu | Gln | Phe | Gln | Ala | Phe | Arg | Asn | Glu | Val | Ala | Val | Leu | Arg | Lys | Thr |
| 385 | | | | | 390 | | | | | 395 | | | | | 400 |
| Arg | His | Val | Asn | Ile | Leu | Leu | Phe | Met | Gly | Tyr | Met | Thr | Lys | Asp | Asn |
| | | | | 405 | | | | | 410 | | | | | 415 | |
| Leu | Ala | Ile | Val | Thr | Gln | Trp | Cys | Glu | Gly | Ser | Ser | Leu | Tyr | Lys | His |
| | | | 420 | | | | | 425 | | | | | 430 | | |
| Leu | His | Val | Gln | Glu | Thr | Lys | Phe | Gln | Met | Phe | Gln | Leu | Ile | Asp | Ile |
| | | 435 | | | | | 440 | | | | | 445 | | | |
| Ala | Arg | Gln | Thr | Ala | Gln | Gly | Met | Asp | Tyr | Leu | His | Ala | Lys | Asn | Ile |
| | 450 | | | | | 455 | | | | | 460 | | | | |
| Ile | His | Arg | Asp | Met | Lys | Ser | Asn | Asn | Ile | Phe | Leu | His | Glu | Gly | Leu |
| 465 | | | | | 470 | | | | | 475 | | | | | 480 |
| Thr | Val | Lys | Ile | Gly | Asp | Phe | Gly | Leu | Ala | Thr | Val | Lys | Ser | Arg | Trp |
| | | | | 485 | | | | | 490 | | | | | 495 | |
| Ser | Gly | Ser | Gln | Gln | Val | Glu | Gln | Pro | Thr | Gly | Ser | Val | Leu | Trp | Met |
| | | | 500 | | | | | 505 | | | | | 510 | | |
| Ala | Pro | Glu | Val | Ile | Arg | Met | Gln | Asp | Asn | Asn | Pro | Phe | Ser | Phe | Gln |
| | | 515 | | | | | 520 | | | | | 525 | | | |
| Ser | Asp | Val | Tyr | Ser | Tyr | Gly | Ile | Val | Leu | Tyr | Glu | Leu | Met | Thr | Gly |
| | 530 | | | | | 535 | | | | | 540 | | | | |
| Glu | Leu | Pro | Tyr | Ser | His | Ile | Asn | Asn | Arg | Asp | Gln | Ile | Ile | Phe | Met |
| 545 | | | | | 550 | | | | | 555 | | | | | 560 |
| Val | Gly | Arg | Gly | Tyr | Ala | Ser | Pro | Asp | Leu | Ser | Lys | Leu | Tyr | Lys | Asn |
| | | | | 565 | | | | | 570 | | | | | 575 | |
| Cys | Pro | Lys | Ala | Met | Lys | Arg | Leu | Val | Ala | Asp | Cys | Val | Lys | Lys | Val |
| | | | 580 | | | | | 585 | | | | | 590 | | |
| Lys | Glu | Glu | Arg | Pro | Leu | Phe | Pro | Gln | Ile | Leu | Ser | Ser | Ile | Glu | Leu |
| | | 595 | | | | | 600 | | | | | 605 | | | |
| Leu | Gln | His | Ser | Leu | Pro | Lys | Ile | Asn | Arg | Ser | Ala | Ser | Glu | Pro | Ser |
| | 610 | | | | | 615 | | | | | 620 | | | | |
| Leu | His | Arg | Ala | Ala | His | Thr | Glu | Asp | Ile | Asn | Ala | Cys | Thr | Leu | Thr |
| 625 | | | | | 630 | | | | | 635 | | | | | 640 |

Thr Ser Pro Arg Leu Pro Val Phe
                645

(2) INFORMATION FOR SEQ ID NO:3:

(i) SEQUENCE CHARACTERISTICS:
      (A) LENGTH: 197 amino acids
      (B) TYPE: amino acid
      (D) TOPOLOGY: linear (ii) MOLECULE TYPE: protein (v) FRAGMENT TYPE: N-terminal (vi) ORIGINAL SOURCE:
      (A) ORGANISM: Homo sapiens (xi) SEQUENCE DESCRIPTION: SEQ ID NO:3:

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
            165                 170                 175

Ser Thr Lys Val Pro Thr Met Cys Val Asp Trp Ser Asn Ile Arg Gln
            180                 185                 190

Leu Leu Leu Phe Pro
        195

(2) INFORMATION FOR SEQ ID NO:4:

(i) SEQUENCE CHARACTERISTICS:
      (A) LENGTH: 147 amino acids
      (B) TYPE: amino acid
      (D) TOPOLOGY: linear (ii) MOLECULE TYPE: peptide (iii) HYPOTHETICAL: NO (v) FRAGMENT TYPE: internal (vi) ORIGINAL SOURCE:
      (A) ORGANISM: Homo sapiens (xi) SEQUENCE DESCRIPTION: SEQ ID NO:4:

Asp Trp Ser Asn Ile Arg Gln Leu Leu Leu Phe Pro Asn Ser Thr Ile

```
  1               5                         10                        15
Gly  Asp  Ser  Gly  Val  Pro  Ala  Leu  Pro  Ser  Leu  Thr  Met  Arg  Arg  Met
               20                      25                    30

Arg  Glu  Ser  Val  Ser  Arg  Met  Pro  Val  Ser  Ser  Gln  His  Arg  Tyr  Ser
          35                      40                        45

Thr  Pro  His  Ala  Phe  Thr  Phe  Asn  Thr  Ser  Ser  Pro  Ser  Ser  Glu  Gly
     50                      55                        60

Ser  Leu  Ser  Gln  Arg  Gln  Arg  Ser  Thr  Ser  Thr  Pro  Asn  Val  His  Met
65                       70                  75                              80

Val  Ser  Thr  Thr  Leu  Pro  Val  Asp  Ser  Arg  Met  Ile  Glu  Asp  Ala  Ile
                ようじ85                      90                        95

Arg  Ser  His  Ser  Glu  Ser  Ala  Ser  Pro  Ser  Ala  Leu  Ser  Ser  Ser  Pro
               100                     105                      110

Asn  Asn  Leu  Ser  Pro  Thr  Gly  Trp  Ser  Gln  Pro  Lys  Thr  Pro  Val  Pro
          115                     120                      125

Ala  Gln  Arg  Glu  Arg  Ala  Pro  Val  Ser  Gly  Thr  Gln  Glu  Lys  Asn  Lys
     130                     135                      140

Ile  Arg  Pro
145
```

(2) INFORMATION FOR SEQ ID NO:5:

(i) SEQUENCE CHARACTERISTICS:
        (A) LENGTH: 346 amino acids
        (B) TYPE: amino acid
        (D) TOPOLOGY: linear (ii) MOLECULE TYPE: peptide (iii) HYPOTHETICAL: NO (v) FRAGMENT TYPE: C-terminal (vi) ORIGINAL SOURCE:
        (A) ORGANISM: Homo sapiens (xi) SEQUENCE DESCRIPTION: SEQ ID NO:5:

```
Thr  Gly  Trp  Ser  Gln  Pro  Lys  Thr  Pro  Val  Pro  Ala  Gln  Arg  Glu  Arg
1                   5                      10                       15

Ala  Pro  Val  Ser  Gly  Thr  Gln  Glu  Lys  Asn  Lys  Ile  Arg  Pro  Arg  Gly
               20                     25                       30

Gln  Arg  Asp  Ser  Ser  Tyr  Tyr  Trp  Glu  Ile  Glu  Ala  Ser  Glu  Val  Met
          35                     40                        45

Leu  Ser  Thr  Arg  Ile  Gly  Ser  Gly  Ser  Phe  Gly  Thr  Val  Tyr  Lys  Gly
     50                     55                       60

Lys  Trp  His  Gly  Asp  Val  Ala  Val  Lys  Ile  Leu  Lys  Val  Val  Asp  Pro
65                      70                    75                              80

Thr  Pro  Glu  Gln  Phe  Gln  Ala  Phe  Arg  Asn  Glu  Val  Ala  Val  Leu  Arg
                    85                    90                         95

Lys  Thr  Arg  His  Val  Asn  Ile  Leu  Leu  Phe  Met  Gly  Tyr  Met  Thr  Lys
               100                    105                       110

Asp  Asn  Leu  Ala  Ile  Val  Thr  Gln  Trp  Cys  Glu  Gly  Ser  Ser  Leu  Tyr
          115                    120                       125

Lys  His  Leu  His  Val  Gln  Glu  Thr  Lys  Phe  Gln  Met  Phe  Gln  Leu  Ile
     130                    135                      140

Asp  Ile  Ala  Arg  Gln  Thr  Ala  Gln  Gly  Met  Asp  Tyr  Leu  His  Ala  Lys
145                     150                   155                            160

Asn  Ile  Ile  His  Arg  Asp  Met  Lys  Ser  Asn  Asn  Ile  Phe  Leu  His  Glu
                    165                   170                         175
```

| | | | | | | | | | | | | | | |
|---|---|---|---|---|---|---|---|---|---|---|---|---|---|---|
|Gly|Leu|Thr|Val<br>180|Lys|Ile|Gly|Asp|Phe<br>185|Gly|Leu|Ala|Thr|Val<br>190|Lys|Ser|
|Arg|Trp|Ser<br>195|Gly|Ser|Gln|Gln|Val<br>200|Glu|Gln|Pro|Thr|Gly<br>205|Ser|Val|Leu|
|Trp|Met<br>210|Ala|Pro|Glu|Val|Ile<br>215|Arg|Met|Gln|Asp|Asn<br>220|Asn|Pro|Phe|Ser|
|Phe<br>225|Gln|Ser|Asp|Val|Tyr<br>230|Ser|Tyr|Gly|Ile|Val<br>235|Leu|Tyr|Glu|Leu|Met<br>240|
|Thr|Gly|Glu|Leu|Pro<br>245|Tyr|Ser|His|Ile|Asn<br>250|Asn|Arg|Asp|Gln|Ile<br>255|Ile|
|Phe|Met|Val|Gly<br>260|Arg|Gly|Tyr|Ala|Ser<br>265|Pro|Asp|Leu|Ser|Lys<br>270|Leu|Tyr|
|Lys|Asn|Cys<br>275|Pro|Lys|Ala|Met|Lys<br>280|Arg|Leu|Val|Ala|Asp<br>285|Cys|Val|Lys|
|Lys|Val<br>290|Lys|Glu|Glu|Arg|Pro<br>295|Leu|Phe|Pro|Gln|Ile<br>300|Leu|Ser|Ser|Ile|
|Glu<br>305|Leu|Leu|Gln|His|Ser<br>310|Leu|Pro|Lys|Ile|Asn<br>315|Arg|Ser|Ala|Ser|Glu<br>320|
|Pro|Ser|Leu|His|Arg<br>325|Ala|Ala|His|Thr|Glu<br>330|Asp|Ile|Asn|Ala|Cys<br>335|Thr|
|Leu|Thr|Thr|Ser<br>340|Pro|Arg|Leu|Pro|Val<br>345|Phe| | | | | |

(2) INFORMATION FOR SEQ ID NO:6:

(i) SEQUENCE CHARACTERISTICS:
        (A) LENGTH: 1213 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Homo sapiens (ix) FEATURE:
        (A) NAME/KEY: CDS
        (B) LOCATION: 373..1113

(xi) SEQUENCE DESCRIPTION: SEQ ID NO:6:

```
TACCGCCACC GCCGCCGCCG ATTCCGGAGC CGGGGTAGTC GCCGCCGCCG CCGCCGCCGC      60

TGCAGCCACT GCAGGCACCG CTGCCGCCGC CTGAGTAGTG TACCGCCACC GCCGCCGCCG     120

ATTCCGGAGC CGGGGTAGTC GCCGCCGCCG CCGCCGCCGC TGCAGCCACT GCAGGCACCG     180

CTGCCGCCGC CTGAGTAGTG GGCTTAGGAA GGAAGAGGTC ATCTCGCTCG GAGCTTCGCT     240

CGGAAGGGTC TTTGTTCCCT GCAGCCCTCC CACGGCAGAG TCTCCAGAGA TTTGGGCCGC     300

TACAAAAAGT GCATTTGCC  CATTCGGCTG TGGATAGAGA AGCAGGAAGA GCACTGGACT     360

TGGAGTCAGG GA ATG ACA ATG GAT AAA AGT GAG CTG GTA CAG AAA GCC        408
              Met Thr Met Asp Lys Ser Glu Leu Val Gln Lys Ala
               1               5                   10

AAA CTC GCT GAG CAG GCT GAG CGC TAT GAT GAT ATG GCT GCA GCC ATG      456
Lys Leu Ala Glu Gln Ala Glu Arg Tyr Asp Asp Met Ala Ala Ala Met
         15                  20                  25

AAG GCA GTC ACA GAA CAG GGG CAT GAA CTC TCC AAC GAA GAG AGA AAT      504
Lys Ala Val Thr Glu Gln Gly His Glu Leu Ser Asn Glu Glu Arg Asn
     30                  35                  40
```

-continued

| | | | | | | | | | | | | | | | | |
|---|---|---|---|---|---|---|---|---|---|---|---|---|---|---|---|---|
| CTG | CTC | TCT | GTT | GCC | TAC | AAG | AAT | GTG | GTA | GGC | GCC | CGC | CGC | TCT | TCC | 552 |
| Leu | Leu | Ser | Val | Ala | Tyr | Lys | Asn | Val | Val | Gly | Ala | Arg | Arg | Ser | Ser | |
| 45 | | | | 50 | | | | | 55 | | | | | | 60 | |
| TGG | CGT | GTC | ATC | TCC | AGC | ATT | GAG | CAG | AAA | ACA | GAG | AGG | AAT | GAG | AAG | 600 |
| Trp | Arg | Val | Ile | Ser | Ser | Ile | Glu | Gln | Lys | Thr | Glu | Arg | Asn | Glu | Lys | |
| | | | | 65 | | | | | 70 | | | | | 75 | | |
| AAG | CAG | CAG | ATG | GGC | AAA | GAG | TAC | CGT | GAG | AAG | ATA | GAG | GCA | GAA | CTG | 648 |
| Lys | Gln | Gln | Met | Gly | Lys | Glu | Tyr | Arg | Glu | Lys | Ile | Glu | Ala | Glu | Leu | |
| | | | 80 | | | | | 85 | | | | | 90 | | | |
| CAG | GAC | ATC | TGC | AAT | GAT | GTT | CTG | GAG | CTG | TTG | GAC | AAA | TAT | CTT | ATT | 696 |
| Gln | Asp | Ile | Cys | Asn | Asp | Val | Leu | Glu | Leu | Leu | Asp | Lys | Tyr | Leu | Ile | |
| | | 95 | | | | | 100 | | | | | 105 | | | | |
| CCC | AAT | GCT | ACA | CAA | CCA | GAA | AGT | AAG | GTG | TTC | TAC | TTG | AAA | ATG | AAA | 744 |
| Pro | Asn | Ala | Thr | Gln | Pro | Glu | Ser | Lys | Val | Phe | Tyr | Leu | Lys | Met | Lys | |
| | 110 | | | | | 115 | | | | | 120 | | | | | |
| GGA | GAT | TAT | TTT | AGG | TAT | CTT | TCT | GAA | GTG | GCA | TCT | GGA | GAC | AAC | AAA | 792 |
| Gly | Asp | Tyr | Phe | Arg | Tyr | Leu | Ser | Glu | Val | Ala | Ser | Gly | Asp | Asn | Lys | |
| 125 | | | | | 130 | | | | | 135 | | | | | 140 | |
| CAA | ACC | ACT | GTG | TCG | AAC | TCC | CAG | CAG | GCT | TAC | CAG | GAA | GCA | TTT | GAA | 840 |
| Gln | Thr | Thr | Val | Ser | Asn | Ser | Gln | Gln | Ala | Tyr | Gln | Glu | Ala | Phe | Glu | |
| | | | | 145 | | | | | 150 | | | | | 155 | | |
| ATT | AGT | AAG | AAA | GAA | ATG | CAG | CCT | ACA | CAC | CCA | ATT | CGT | CTT | GGT | CTG | 888 |
| Ile | Ser | Lys | Lys | Glu | Met | Gln | Pro | Thr | His | Pro | Ile | Arg | Leu | Gly | Leu | |
| | | | 160 | | | | | 165 | | | | | 170 | | | |
| GCA | CTA | AAT | TTC | TCA | GTC | TTT | TAC | TAT | GAG | ATT | CTA | AAC | TCT | CCT | GAA | 936 |
| Ala | Leu | Asn | Phe | Ser | Val | Phe | Tyr | Tyr | Glu | Ile | Leu | Asn | Ser | Pro | Glu | |
| | | 175 | | | | | 180 | | | | | 185 | | | | |
| AAG | GCC | TGT | AGC | CTG | GCA | AAA | ACG | GCA | TTT | GAT | GAA | GCA | ATT | GCT | GAA | 984 |
| Lys | Ala | Cys | Ser | Leu | Ala | Lys | Thr | Ala | Phe | Asp | Glu | Ala | Ile | Ala | Glu | |
| | 190 | | | | | 195 | | | | | 200 | | | | | |
| TTG | GAT | ACG | CTG | AAT | GAA | GAG | TCT | TAT | AAA | GAC | AGC | ACT | CTG | ATC | ATG | 1032 |
| Leu | Asp | Thr | Leu | Asn | Glu | Glu | Ser | Tyr | Lys | Asp | Ser | Thr | Leu | Ile | Met | |
| 205 | | | | | 210 | | | | | 215 | | | | | 220 | |
| CAG | TTA | CTT | AGG | GAC | AAT | CTC | ACT | CTG | TGG | ACA | TCG | GAA | AAC | CAG | GGA | 1080 |
| Gln | Leu | Leu | Arg | Asp | Asn | Leu | Thr | Leu | Trp | Thr | Ser | Glu | Asn | Gln | Gly | |
| | | | | 225 | | | | | 230 | | | | | 235 | | |
| GAC | GAA | GGA | GAC | GCT | GGG | GAG | GGA | GAG | AAC | TAATGTTTCT | CGTGCTTTGT | | | | | 1130 |
| Asp | Glu | Gly | Asp | Ala | Gly | Glu | Gly | Glu | Asn | | | | | | | |
| | | | 240 | | | | | 245 | | | | | | | | |

GATCTGTCCA GTGTCACTCT GTACCCTCAA CATATATCCC TTGTGCGATA AAAAAAAAA  1190

AAAAAAAAAA AAAAAAAAAA AAA  1213

( 2 ) INFORMATION FOR SEQ ID NO:7:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Thr | Met | Asp | Lys | Ser | Glu | Leu | Val | Gln | Lys | Ala | Lys | Leu | Ala | Glu |
|---|---|---|---|---|---|---|---|---|---|---|---|---|---|---|---|
| 1 | | | | 5 | | | | | 10 | | | | | 15 | |
| Gln | Ala | Glu | Arg | Tyr | Asp | Asp | Met | Ala | Ala | Ala | Met | Lys | Ala | Val | Thr |
| | | | 20 | | | | | 25 | | | | | 30 | | |
| Glu | Gln | Gly | His | Glu | Leu | Ser | Asn | Glu | Glu | Arg | Asn | Leu | Leu | Ser | Val |
| | | | 35 | | | | | 40 | | | | | 45 | | |
| Ala | Tyr | Lys | Asn | Val | Val | Gly | Ala | Arg | Arg | Ser | Ser | Trp | Arg | Val | Ile |
| | 50 | | | | | 55 | | | | | 60 | | | | |

| Ser | Ser | Ile | Glu | Gln | Lys | Thr | Glu | Arg | Asn | Glu | Lys | Lys | Gln | Gln | Met |
| 65 | | | | | 70 | | | | | 75 | | | | | 80 |

| Gly | Lys | Glu | Tyr | Arg | Glu | Lys | Ile | Glu | Ala | Glu | Leu | Gln | Asp | Ile | Cys |
| | | | | 85 | | | | | 90 | | | | | 95 | |

| Asn | Asp | Val | Leu | Glu | Leu | Leu | Asp | Lys | Tyr | Leu | Ile | Pro | Asn | Ala | Thr |
| | | | 100 | | | | | 105 | | | | | 110 | | |

| Gln | Pro | Glu | Ser | Lys | Val | Phe | Tyr | Leu | Lys | Met | Lys | Gly | Asp | Tyr | Phe |
| | | 115 | | | | | 120 | | | | | 125 | | | |

| Arg | Tyr | Leu | Ser | Glu | Val | Ala | Ser | Gly | Asp | Asn | Lys | Gln | Thr | Thr | Val |
| | 130 | | | | | 135 | | | | | 140 | | | | |

| Ser | Asn | Ser | Gln | Gln | Ala | Tyr | Gln | Glu | Ala | Phe | Glu | Ile | Ser | Lys | Lys |
| 145 | | | | | 150 | | | | | 155 | | | | | 160 |

| Glu | Met | Gln | Pro | Thr | His | Pro | Ile | Arg | Leu | Gly | Leu | Ala | Leu | Asn | Phe |
| | | | | 165 | | | | | 170 | | | | | 175 | |

| Ser | Val | Phe | Tyr | Tyr | Glu | Ile | Leu | Asn | Ser | Pro | Glu | Lys | Ala | Cys | Ser |
| | | | 180 | | | | | 185 | | | | | 190 | | |

| Leu | Ala | Lys | Thr | Ala | Phe | Asp | Glu | Ala | Ile | Ala | Glu | Leu | Asp | Thr | Leu |
| | | 195 | | | | | 200 | | | | | 205 | | | |

| Asn | Glu | Glu | Ser | Tyr | Lys | Asp | Ser | Thr | Leu | Ile | Met | Gln | Leu | Leu | Arg |
| | 210 | | | | | 215 | | | | | 220 | | | | |

| Asp | Asn | Leu | Thr | Leu | Trp | Thr | Ser | Glu | Asn | Gln | Gly | Asp | Glu | Gly | Asp |
| 225 | | | | | 230 | | | | | 235 | | | | | 240 |

| Ala | Gly | Glu | Gly | Glu | Asn |
| | | | | 245 | |

( 2 ) INFORMATION FOR SEQ ID NO:8:

( i ) SEQUENCE CHARACTERISTICS:
        ( A ) LENGTH: 2834 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens ( i x ) FEATURE:
        ( A ) NAME/KEY: CDS
        ( B ) LOCATION: 85..822

( x i ) SEQUENCE DESCRIPTION: SEQ ID NO:8:

```
GCCCACTCCC ACCGCCAGCT GGAACCCTGG GGACTACGAC GTCCCTCAAA CCTTGCTTCT              60

AGGAGATAAA AAGAACATCC AGTC ATG GAT AAA AAT GAG CTG GTT CAG AAG              111
                          Met Asp Lys Asn Glu Leu Val Gln Lys
                           1               5

GCC AAA CTG GCC GAG CAG GCT GAG CGA TAT GAT GAC ATG GCA GCC TGC              159
Ala Lys Leu Ala Glu Gln Ala Glu Arg Tyr Asp Asp Met Ala Ala Cys
 10              15                  20                  25

ATG AAG TCT GTA ACT GAG CAA GGA GCT GAA TTA TCC AAT GAG GAG AGG              207
Met Lys Ser Val Thr Glu Gln Gly Ala Glu Leu Ser Asn Glu Glu Arg
                 30                  35                  40

AAT CTT CTC TCA GTT GCT TAT AAA AAT GTT GTA GGA GCC CGT AGG TCA              255
Asn Leu Leu Ser Val Ala Tyr Lys Asn Val Val Gly Ala Arg Arg Ser
                 45                  50                  55

TCT TGG AGG GTC GTC TCA AGT ATT GAA CAA AAG ACG GAA GGT GCT GAG              303
Ser Trp Arg Val Val Ser Ser Ile Glu Gln Lys Thr Glu Gly Ala Glu
         60                  65                  70
```

| AAA<br>Lys<br>75 | AAA<br>Lys | CAG<br>Gln | CAG<br>Gln | ATG<br>Met | GCT<br>Ala<br>80 | CGA<br>Arg | GAA<br>Glu | TAC<br>Tyr | AGA<br>Arg | GAG<br>Glu<br>85 | AAA<br>Lys | ATT<br>Ile | GAG<br>Glu | ACG<br>Thr | GAG<br>Glu | 351 |
|---|---|---|---|---|---|---|---|---|---|---|---|---|---|---|---|---|
| CTA<br>Leu<br>90 | AGA<br>Arg | GAT<br>Asp | ATC<br>Ile | TGC<br>Cys | AAT<br>Asn<br>95 | GAT<br>Asp | GTA<br>Val | CTG<br>Leu | TCT<br>Ser | CTT<br>Leu<br>100 | TTG<br>Leu | GAA<br>Glu | AAG<br>Lys | TTC<br>Phe | TTG<br>Leu<br>105 | 399 |
| ATC<br>Ile | CCC<br>Pro | AAT<br>Asn | GCT<br>Ala | TCA<br>Ser<br>110 | CAA<br>Gln | GCA<br>Ala | GAG<br>Glu | AGC<br>Ser | AAA<br>Lys<br>115 | GTC<br>Val | TTC<br>Phe | TAT<br>Tyr | TTG<br>Leu | AAA<br>Lys<br>120 | ATG<br>Met | 447 |
| AAA<br>Lys | GGA<br>Gly | GAT<br>Asp | TAC<br>Tyr<br>125 | TAC<br>Tyr | CGT<br>Arg | TAC<br>Tyr | TTG<br>Leu | GCT<br>Ala<br>130 | GAG<br>Glu | GTT<br>Val | GCC<br>Ala | GCT<br>Ala | GGT<br>Gly<br>135 | GAT<br>Asp | GAC<br>Asp | 495 |
| AAG<br>Lys | AAA<br>Lys | GGG<br>Gly<br>140 | ATT<br>Ile | GTC<br>Val | GAT<br>Asp | CAG<br>Gln | TCA<br>Ser<br>145 | CAA<br>Gln | CAA<br>Gln | GCA<br>Ala | TAC<br>Tyr | CAA<br>Gln<br>150 | GAA<br>Glu | GCT<br>Ala | TTT<br>Phe | 543 |
| GAA<br>Glu | ATC<br>Ile<br>155 | AGC<br>Ser | AAA<br>Lys | AAG<br>Lys | GAA<br>Glu | ATG<br>Met<br>160 | CAA<br>Gln | CCA<br>Pro | ACA<br>Thr | CAT<br>His | CCT<br>Pro<br>165 | ATC<br>Ile | AGA<br>Arg | CTG<br>Leu | GGT<br>Gly | 591 |
| CTG<br>Leu<br>170 | GCC<br>Ala | CTT<br>Leu | AAC<br>Asn | TTC<br>Phe | TCT<br>Ser<br>175 | GTG<br>Val | TTC<br>Phe | TAT<br>Tyr | TAT<br>Tyr | GAG<br>Glu<br>180 | ATT<br>Ile | CTG<br>Leu | AAC<br>Asn | TCC<br>Ser | CCA<br>Pro<br>185 | 639 |
| GAG<br>Glu | AAA<br>Lys | GCC<br>Ala | TGC<br>Cys | TCT<br>Ser<br>190 | CTT<br>Leu | GCA<br>Ala | AAG<br>Lys | ACA<br>Thr | GCT<br>Ala<br>195 | TTT<br>Phe | GAT<br>Asp | GAA<br>Glu | GCC<br>Ala | ATT<br>Ile<br>200 | GCT<br>Ala | 687 |
| GAA<br>Glu | CTT<br>Leu | GAT<br>Asp | ACA<br>Thr<br>205 | TTA<br>Leu | AGT<br>Ser | GAA<br>Glu | GAG<br>Glu | TCA<br>Ser<br>210 | TAC<br>Tyr | AAA<br>Lys | GAC<br>Asp | AGC<br>Ser | ACG<br>Thr<br>215 | CTA<br>Leu | ATA<br>Ile | 735 |
| ATG<br>Met | CAA<br>Gln | TTA<br>Leu<br>220 | CTG<br>Leu | AGA<br>Arg | GAC<br>Asp | AAC<br>Asn | TTG<br>Leu<br>225 | ACA<br>Thr | TTG<br>Leu | TGG<br>Trp | ACA<br>Thr | TCG<br>Ser<br>230 | GAT<br>Asp | ACC<br>Thr | CAA<br>Gln | 783 |
| GGA<br>Gly | GAC<br>Asp<br>235 | GAA<br>Glu | GCT<br>Ala | GAA<br>Glu | GCA<br>Ala | GGA<br>Gly<br>240 | GAA<br>Glu | GGA<br>Gly | GGG<br>Gly | GAA<br>Glu | AAT<br>Asn<br>245 | TAACCGGCCT | | | | 829 |

| | |
|---|---|
| TCCAACTTTT GTCTGCCTCA TTCTAAAATT TACACAGTAG ACCATTTGTC ATCCATGCTG | 889 |
| TCCCACAAAT AGTTTTTGT TTACGATTTA TGACAGGTTT ATGTTACTTC TATTTGAATT | 949 |
| TCTATATTTC CCATGTGGTT TTTATGTTTA ATATTAGGGG AGTAGAGCCA GTTAACATTT | 1009 |
| AGGGAGTTAT CTGTTTTCAT CTTGAGGTGG CCAATATGGG GATGTGGAAT TTTTATACAA | 1069 |
| GTTATAAGTG TTTGGCATAG TACTTTTGGT ACATTGTGGC TTCAAAGGG CCAGTGTAAA | 1129 |
| ACTGCTTCCA TGTCTAAGCA AGAAAACTG CCTACATACT GGTTTGTCCT GGCGGGGAAT | 1189 |
| AAAAGGGATC ATTGGTTCCA GTCACAGGTG TAGTAATTGT GGGTACTTTA AGGTTTGGAG | 1249 |
| CACTTACAAG GCTGTGGTAG AATCATACCC CATGGATACC ACATATTAAA CCATGTATAT | 1309 |
| CTGTGGAATA CTCAATGTGT ACACCTTTGA CTACAGCTGC AGAAGTGTTC CTTTAGACAA | 1369 |
| AGTTGTGACC CATTTTACTC TGGATAAGGG CAGAAACGGT TCACATTCCA TTATTTGTAA | 1429 |
| AGTTACCTGC TGTTAGCTTT CATTATTTTT GCTACACTCA TTTTATTTGT ATTTAAATGT | 1489 |
| TTTAGGCAAC CTAAGAACAA ATGTAAAAGT AAAGATGCAG GAAAAATGAA TTGCTTGGTA | 1549 |
| TTCATTACTT CATGTATATC AAGCACAGCA GTAAAACAAA ACCCATGTA TTTAACTTTT | 1609 |
| TTTTAGGATT TTTGCTTTTG TGATTTTTTT TTTTTTTTT TGATACTTGC CTAACATGCA | 1669 |
| TGTGCTGTAA AAATAGTTAA CAGGGAAATA ACTTGAGATG ATGGCTAGCT TTGTTTAATG | 1729 |
| TCTTATGAAA TTTTCATGAA CAATCCAAGC ATAATTGTTA AGAACACGTG TATTAAATTC | 1789 |
| ATGTAAGTGG AATAAAAGTT TTATGAATGG ACTTTTCAAC TACTTTCTCT ACAGCTTTTC | 1849 |
| ATGTAAATTA GTCTTGGTTC TGAAACTTCT CTAAAGGAAA TTGTACATTC TTTGAAATTT | 1909 |

-continued

| | | | | | |
|---|---|---|---|---|---|
| ATTCCTTATT | CCCTCTTGGC | AGCTAATGGG | CTCTTACCAA | GTTTAAACAC | AAAATTTATC | 1969
| ATAACAAAAA | TACTACTAAT | ATAACTACTG | TTTCCATGTC | CCATGATCCC | CTCTCTTCCT | 2029
| CCCCACCCTG | AAAAAAATGA | GTTCCTATTT | TTTCTGGGAG | AGGGGGGGAT | TGATTAGAAA | 2089
| AAAATGTAGT | GTGTTCCATT | TAAAATTTTG | GCATATGGCA | TTTTCTAACT | TAGGAAGCCA | 2149
| CAATGTTCTT | GGCCCATCAT | GACATTGGGT | AGCATTAACT | GTAAGTTTTG | TGCTTCCAAA | 2209
| TCACTTTTTG | GTTTTAAGA | ATTTCTTGAT | ACTCTTATAG | CCTGCCTTCA | ATTTTGATCC | 2269
| TTTATTCTTT | CTATTTGTCA | GGTGCACAAG | ATTACCTTCC | TGTTTTAGCC | TTCTGTCTTG | 2329
| TCACCAACCA | TTCTTACTTG | GTGGCCATGT | ACTTGGAAAA | AGGCCGCATG | ATCTTTCTGG | 2389
| CTCCACTCAG | TGTCTAAGGC | ACCCTGCTTC | CTTTGCTTGC | ATCCCACAGA | CTATTTCCCT | 2449
| CATCCTATTT | ACTGCAGCAA | ATCTCTCCTT | AGTTGATGAG | ACTGTGTTTA | TCTCCCTTTA | 2509
| AAACCCTACC | TATCCTGAAT | GGTCTGTCAT | TGTCTGCCTT | TAAAATCCTT | CCTCTTTCTT | 2569
| CCTCCTCTAT | TCTCTAAATA | ATGATGGGGC | TAAGTTATAC | CCAAAGCTCA | CTTTACAAAA | 2629
| TATTTCCTCA | GTACTTTGCA | GAAAACACCA | AACAAAAATG | CCATTTTAAA | AAAGGTGTAT | 2689
| TTTTTCTTTT | AGAATGTAAG | CTCCTCAAGA | GCAGGGACAA | TGTTTTCTGT | ATGTTCTATT | 2749
| GTGCCTAGTA | CACTGTAAAT | GCTCAATAAA | TATTGATGAT | GGGAGGCAGT | GAGTCTTGAT | 2809
| GATAAGGGTG | AGAAACTGAA | ATCCC | | | | 2834

( 2 ) INFORMATION FOR SEQ ID NO:9:

( i ) SEQUENCE CHARACTERISTICS:
        ( A ) LENGTH: 245 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Asp Lys Asn Glu Leu Val Gln Lys Ala Lys Leu Ala Glu Gln Ala
 1               5                  10                  15
Glu Arg Tyr Asp Asp Met Ala Ala Cys Met Lys Ser Val Thr Glu Gln
                20                  25                  30
Gly Ala Glu Leu Ser Asn Glu Glu Arg Asn Leu Leu Ser Val Ala Tyr
            35                  40                  45
Lys Asn Val Val Gly Ala Arg Arg Ser Ser Trp Arg Val Val Ser Ser
    50                  55                  60
Ile Glu Gln Lys Thr Glu Gly Ala Glu Lys Lys Gln Gln Met Ala Arg
 65                  70                  75                  80
Glu Tyr Arg Glu Lys Ile Glu Thr Glu Leu Arg Asp Ile Cys Asn Asp
                85                  90                  95
Val Leu Ser Leu Leu Glu Lys Phe Leu Ile Pro Asn Ala Ser Gln Ala
           100                 105                 110
Glu Ser Lys Val Phe Tyr Leu Lys Met Lys Gly Asp Tyr Tyr Arg Tyr
           115                 120                 125
Leu Ala Glu Val Ala Ala Gly Asp Asp Lys Lys Gly Ile Val Asp Gln
           130                 135                 140
Ser Gln Gln Ala Tyr Gln Glu Ala Phe Glu Ile Ser Lys Lys Glu Met
145                 150                 155                 160
Gln Pro Thr His Pro Ile Arg Leu Gly Leu Ala Leu Asn Phe Ser Val
                165                 170                 175
Phe Tyr Tyr Glu Ile Leu Asn Ser Pro Glu Lys Ala Cys Ser Leu Ala
                180                 185                 190
```

| | | | | | | | | | | | | | | |
|---|---|---|---|---|---|---|---|---|---|---|---|---|---|---|
| Lys | Thr | Ala 195 | Phe | Asp | Glu | Ala | Ile 200 | Ala | Glu | Leu | Asp 205 | Thr | Leu | Ser | Glu |
| Glu | Ser 210 | Tyr | Lys | Asp | Ser | Thr 215 | Leu | Ile | Met | Gln | Leu 220 | Leu | Arg | Asp | Asn |
| Leu 225 | Thr | Leu | Trp | Thr | Ser 230 | Asp | Thr | Gln | Gly | Asp 235 | Glu | Ala | Glu | Ala | Gly 240 |
| Glu | Gly | Gly | Glu | Asn 245 | | | | | | | | | | | |